(12) United States Patent
    Grissom

(10) Patent No.: US 9,032,963 B2
(45) Date of Patent: May 19, 2015

(54) WRAPS FOR SWADDLING BABIES DURING MEDICAL PROCEDURES AND METHODS OF USING THE SAME

(76) Inventor: Carolyn Grissom, Raleigh, NC (US)

( * ) Notice: Subject to any disclaimer, the term of this patent is extended or adjusted under 35 U.S.C. 154(b) by 516 days.

(21) Appl. No.: 12/547,297

(22) Filed: Aug. 25, 2009

(65) Prior Publication Data

US 2010/0071709 A1    Mar. 25, 2010

Related U.S. Application Data

(60) Provisional application No. 61/190,023, filed on Aug. 25, 2008.

(51) Int. Cl.
 *A61F 5/37* (2006.01)
 *A41B 13/06* (2006.01)
 *A41D 13/12* (2006.01)
 *A47G 9/08* (2006.01)
 *A47G 9/02* (2006.01)

(52) U.S. Cl.
 CPC . *A61F 5/37* (2013.01); *A47G 9/083* (2013.01); *A41D 13/1272* (2013.01); *A47G 9/0223* (2013.01); *A41B 13/06* (2013.01)

(58) Field of Classification Search
 CPC .......... A61F 5/37; A41B 13/00; A41B 13/06; A41B 13/065; A47G 9/02; A47G 9/0207; A47G 9/0223; A47G 9/08; A47G 9/083; A41D 13/1272
 USPC ............. 128/846, 869, 870, 873, 874; 2/69.5, 2/75, 80, 114; 5/482, 494, 413 R; D2/718, 719; D6/603; 604/358, 604/358.01, 385.04
 See application file for complete search history.

(56) References Cited

U.S. PATENT DOCUMENTS

| 1,583,419 | A | * | 5/1926 | Rose Perl ....................... 5/413 R |
| 1,723,644 | A | * | 8/1929 | Collingbourne ................. 2/69.5 |
| 4,979,250 | A | * | 12/1990 | Troncone et al. ................. 5/494 |
| 5,129,406 | A | * | 7/1992 | Magnusen et al. ............ 128/873 |
| 7,003,825 | B1 | * | 2/2006 | Levings ............................ 5/482 |
| 7,254,849 | B1 | * | 8/2007 | Fiebrich et al. ................... 5/482 |
| 2009/0165806 | A1 | * | 7/2009 | Tucker .......................... 128/875 |

* cited by examiner

*Primary Examiner* — Alireza Nia
*Assistant Examiner* — Keri J Nelson
(74) *Attorney, Agent, or Firm* — Bennett Mullinax, LLC

(57) ABSTRACT

Wraps for swaddling babies are provided that include a body having a base side. The wrap can further include two arms that are attached to the base side of the body of the wrap. The arms can extend outward in an opposite direction to one another along the base side of the body of the wrap. Related methods of using the wrap are also provided.

20 Claims, 32 Drawing Sheets

WRAPS FOR SWADDLING BABIES DURING MEDICAL PROCEDURES AND METHODS OF USING THE SAME

RELATED APPLICATIONS

The presently disclosed subject matter claims the benefit of U.S. Provisional Patent Application Ser. No. 61/190,023, filed Aug. 25, 2008, the disclosure of which is incorporated herein by reference in its entirety.

TECHNICAL FIELD

The subject matter disclosed herein relates generally to a wrap. More particularly, the subject matter disclosed herein relates to a wrap that can be used as a swaddling blanket to hold a baby therein for medical observation and/or procedures.

BACKGROUND

Nurses often have to swaddle babies upon whom medical procedures, such as echocardiograms, are being performed as well as babies under medical observations. Swaddling keeps the babies warm and semi-immobile. Further, swaddling babies can keep the babies calm. To swaddle a baby, a square swaddling blanket is folded in half along its diagonal to create a triangular shape with three cornered sides. The baby is laid on the blanket with its head just above the fold in the blanket with a cornered side above each shoulder and one cornered side below the baby's feet. One cornered side of the folded blanket is folded over the shoulder of the baby and tucked around the baby. The cornered side below the feet is then folded up towards the baby and placed over the first folded cornered side, thereby covering the baby's feet. The last cornered side is then folded over the other shoulder and the other folded cornered sides. While the baby is tightly packaged and immobile, the baby's body is inaccessible unless the baby is "unswaddled." A baby swaddled in this manner cannot have medical devices such as a pulse oximeter, which measures the percentage of oxygen in the blood, attached to a finger or toe of the baby during a procedure, such an echocardiogram. Normally, with babies, medical devices such as a pulse oximeter are attached to their toes. However, with a conventional swaddling blanket, the base is folded up over the feet and then wrapped around the body as described above. This configuration covers up the feet and prevents access to the toes.

A need exists for a wrap that allows a baby to be snugly wrapped in a position for the test and also provides easy access to the baby's body where a medical device can be precisely positioned, if desired.

SUMMARY

In accordance with this disclosure, wraps for swaddling babies and related methods are provided. It is, therefore, an object of the present disclosure to provide a wrap that serves as a swaddling blanket that can be used to hold a baby while a medical observation occurs and/or a medical procedure is performed. For example, a wrap that serves as a swaddling blanket can be provided that can be used to hold a baby in a position to permit observations to be conducted and/or medical procedures to be performed. This and other objects as may become apparent from the present disclosure are achieved, at least in whole or in part, by the subject matter described herein.

In one aspect of the present subject matter, a wrap is provided that can include a body with at least one arm attached that extends along a base side of the body. For example, two arms can be attached to the body with the arms being generally planar and extending along the same side of the body. The arms can be about parallel to the side of the body and extend outward in an opposite direction to one another along which they extend. In some embodiments, a neck can extend outward from the side of the body with the at least one arm extending outward from an end of the neck distal from the side of the body.

The body can be different shapes. For example, the body can be rectangular or triangular in shape. For bodies that are triangular in shape, the arms can extend outward and along a base side of the triangular shape. For some embodiments having two arms extending out from the body, the arms can have a combined length that is greater than the length of the side of the body along which the arms extend.

In some embodiments, a strap can be provided that can be wrapped around the wrap once the wrap is folded around the baby. The strap can have a fastener mechanism attached thereto to secure the wrap in place. The end portion of the body distal from the at least one arm can be left unfolded to allow access to the body of the baby to permit attachment of a medical device to the body of the baby, for example, the feet.

The wrap can be a sheet article, such as, for example, fabric or paper. The fabric can be a woven, knit, or nonwoven fabric. It can be made of natural or man-made fibers, yarns or films. Further, the wrap can be disposable or reusable.

In another aspect of the present subject matter, a wrap for swaddling babies is provided. The wrap can comprise a body and a neck extending outward from a side of the body along a central axis of the body such that a proximal end of the neck is integral to the body and a distal end of the neck extends away from the body. The wrap also can include two arms attached to the neck at the distal end of the neck. Each arm extends outward from the neck in an opposite direction along the side of the body.

The body of the wrap can include a triangular shape having three angled corners. The side of the body from which the neck extends can comprise a base side. An angled corner opposite the base side can form an end portion of the body. The remaining angled corners of the body can form peripheral side portions configured to be folded across the body when a baby is placed thereon. The arms can be configured to fold downwardly and diagonally around the body after folding of the peripheral side portions. The arms can be about parallel to the side of the body along which they extend. The arms can have a combined length that is greater than the length of the side of the body along which the arms extend.

A strap can be configured to wrap around the folded body and arms to further secure the peripheral side portions and the arms in their respective folded positions. The strap can have a fastener mechanism attached thereto to secure the wrap in place. The end portion of the body can be configured to be left unfolded upon the folding of the peripheral side portions and the arms to allow access to the body of a baby wrapped within the wrap to permit attachment of a medical device to the body, for example, to a toe of one of the feet.

According to an additional aspect of the present subject matter, a method for swaddling babies during medical procedures and observations is provided. The method can comprise providing a wrap that has a body having a base side and the body having first and second peripheral side portions. The wrap can also include two arms attached to the body along the base side of the body. The arms can extend outward in an opposite direction to one another along the base side of the body. The method also can include placing the wrap in a flat planar position with the arm extending outward in an opposite direction to one another along the base side of the body. A baby can then be placed on the wrap with the shoulders aligned with the arms. The first peripheral side portions can be folded over the baby and the second peripheral side portion can be folded over the first peripheral side portion. The arms can be folded diagonally and downward over the shoulders of the baby and over the first and second peripheral side portions so that the arms of the wrap cross.

The arms of the wrap can be tucked behind the body of the wrap after folding the arms. A strap can be wrapped around the folded body and arms to further secure the peripheral side portions and the arms in their respective folded positions. Also, the arms and the body can include a fastener such that the portion of the fastener on the arms of the wrap can engage the portion of the fastener on the body on a backside of the wrap to secure the wrap around the baby.

According to a further aspect of the present subject matter, a method for swaddling babies during medical procedures and observations is provided. The method can comprise providing a wrap that has a body having a base side and the body having first and second peripheral side portions. The wrap can also include two arms attached to the body along the base side of the body. The arms can extend outward in an opposite direction to one another along the base side of the body. The method also can include placing the wrap in a flat planar position with the arm extending outward in an opposite direction to one another along the base side of the body. A baby can then be placed on the wrap with the shoulders aligned with the arms. The arms can be folded downward over the shoulders of the baby and over the arms of the baby. The arms can then be tucked between the body of the baby and the body of the wrap.

In such a method, the first peripheral side portion of the body can be folded over the baby and the second peripheral side portion of the body can be folded over the first peripheral side portion of the body. A strap can be wrapped around the folded peripheral side portions of the body to further secure the peripheral side portions in their folded positions. Further, if desired, the ends of the folded arms can be pulled in a direction away from the baby to snugly tighten the arms of the wrap around the shoulder and arms of the baby after folding the arms.

An object of the presently disclosed subject matter having been stated hereinabove, and which is achieved in whole or in part by the presently disclosed subject matter, other objects will become evident as the description proceeds when taken in connection with the accompanying drawings as best described hereinbelow.

BRIEF DESCRIPTION OF THE DRAWINGS

A full and enabling disclosure of the present subject matter including the best mode thereof to one of ordinary skill in the art is set forth more particularly in the remainder of the specification, including reference to the accompanying figures, in which.

DETAILED DESCRIPTION

Reference will now be made in detail to the description of the present subject matter, one or more examples of which are shown in the figures. Each example is provided to explain the subject matter and not as a limitation. In fact, features illustrated or described as part of one embodiment can be used in another embodiment to yield still a further embodiment. It is intended that the present subject matter cover such modifications and variations.

Figure 1:
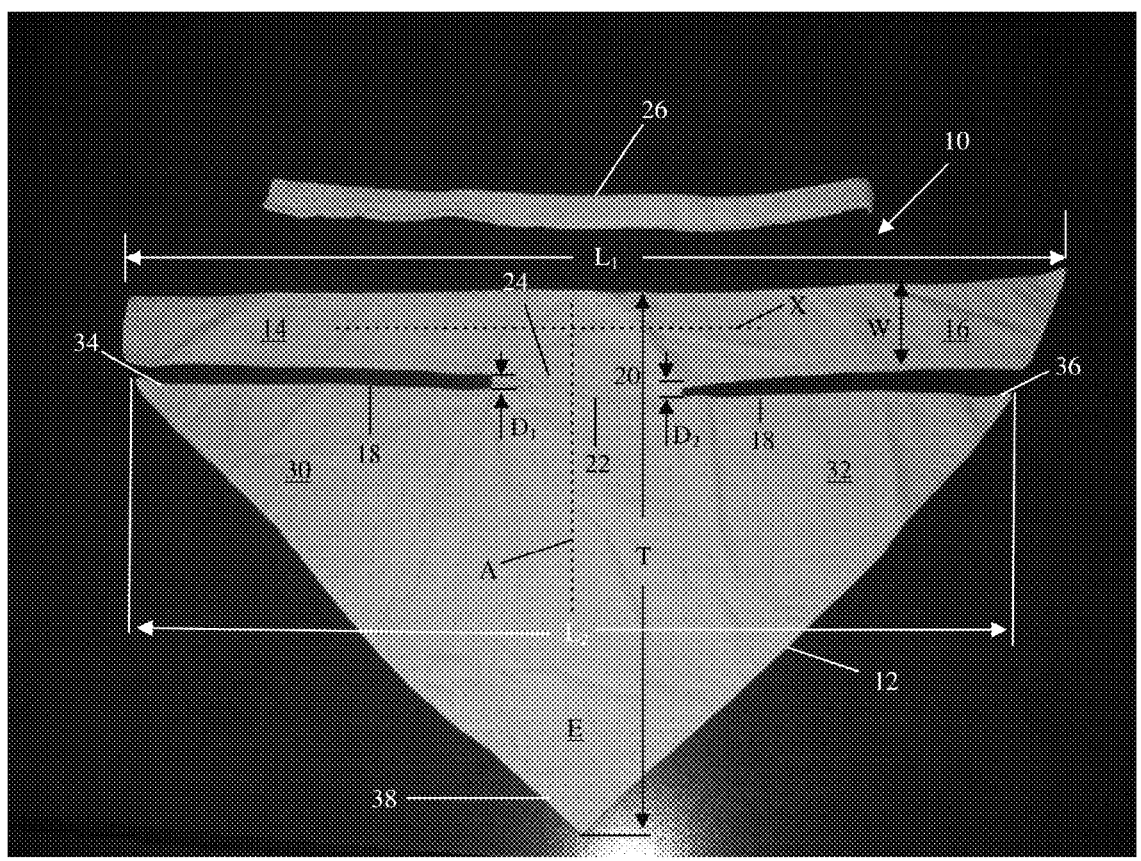
FIG. 1 illustrates a top perspective view of an embodiment of a wrap according to the present subject matter.

FIG. 1 illustrates a wrap, generally designated 10. The wrap 10 can be a sheet article. For example, the wrap 10 can include or be a fabric, a film or paper. In embodiments, where the wrap 10 is a fabric, the fabric can be a woven, knit, or nonwoven fabric. The wrap 10 can include a body 12 with at least one arm, shown for example as arms 14, 16, attached to the body 12 and extending along a side 18 of the body 12. For example, a first arm 14 and a second arm 16 can be attached to the body 12 with the arms 14, 16 being generally planar, i.e., lying within the same plane, along an axis X and extending along the same side 18 of the body 12. The arms 14, 16 can extend about parallel to the side 14 of the body 12 along which they extend.

The arms 14, 16 can reside against the side 18 of the body 12. Thus, the arms 14, 16 can be connected directly to the side 18 of the body 12 without a neck therebetween. Alternatively, the arms 14, 16 can be separated from the body 12. For example, the arms 14, 16 can be separated from the body 12 by a neck 20. The arm 14 can be separated from the side 18 of the body 12 by a distance $D_1$ and the arm 16 can be separated from the side 18 of the body 12 by a distance $D_2$. Distance $D_1$ can be different from distance $D_2$. Alternatively, distance $D_1$ can be the same as distance $D_2$. The distances $D_1$ and $D_2$ can define the width of the neck 20. The distances $D_1$ and $D_2$ can be large or small. For example, the distances $D_1$ and $D_2$ can be up to three inches or more. The distances $D_1$ and $D_2$ can be determined based on the size of the baby intended to be wrap and/or the intended use of the wrap with regards to the medical procedure to be performed. For example, the distances $D_1$ and $D_2$ can be big enough to allow an arm of the baby to extend therethrough while the baby receives a medical device or treatment in that arm.

The neck 20 can extend outward from the side 18 of the body 12. The neck 20 can serve as an attachment point for the arms 14, 16 to the body 12. The neck 20 can generally be centered along the side 18 of the body 12. For example, the neck 20 can be generally centered about an axis A passing through the middle of the body 12. The neck 20 can have an end 22 proximal to the body 12 and an end 24 distal from the body 12. The proximal end 22 of the neck 20 can be integral to the body 12. The arms 14, 16 can extend outward from the end 24 of the neck 20 distal from the side 18 of the body 12.

The combined length $L_1$ of the arms 14, 16 can be greater than the length $L_2$ of the side 18 of the body 12. Alternatively, the combined length $L_1$ of the arms can be shorter than the length $L_2$ of the side 18 of the body 12. The combined length $L_1$ of the arms 14, 16 can also be determined based on the size of the baby intended to be wrap and/or the intended use of the wrap with regards to a medical procedure to be performed. The combined length $L_1$ of the arms 14, 16, however, can be configured to permit a secure wrapping of the wrap around the baby or around the shoulder and arms of the baby. Thus, the combined length $L_1$ of the arms 14, 16 can also vary depending on whether a securement mechanism, such as a strap or fastener is used. Similarly, the length $L_2$ of the side 18 of the body 12 can be determined based on the size of the baby intended to be wrap and/or the intended use of the wrap with regards to the medical procedure to be performed.

The wrap 10 can have an overall width T. The width T can be measured from the sides of the arms 14, 16 distal from the body 12 to an end portion E of the body 12. The width T for a body shape that is triangular as shown in FIG. 1 can be such that it permits the end portion E of the body 12 distal from the arms 14, 16 to be folded upward when a baby is properly placed on the wrap 10 for swaddling. The width T of the wrap 10 can be determined based on the size of the baby intended to be wrap and/or the intended use of the wrap with regards to a medical procedure to be performed.

The body 12 can be any shape that can facilitate swaddling of a baby. For example, the body 12 can be triangular in shape with the arms 14, 16 extending outward and along the side 18, which serves as a base of the triangular shape. The triangular shape can have three angled corners 34, 36, 38 with the side 18 of the body 12 from which the neck 20 extends comprising a base side. The angled corner 38 opposite the base side can form the end portion E of the body 12. The remaining angled corners 34, 36 of the body 12 can form peripheral side portions, or wings, 30, 32 configured to be folded across the body 12 and around the baby B placed on the body 12.

The length $L_2$ of the side 18 of the body 12 can be such that both peripheral side portions 30, 32 can wrap at least partially around a baby that is placed in the middle along the axis A. Further, the length $L_1$ can be such that the arms 14, 16 can be wrapped downward in a diagonal direction around the folded ends so that the arms wrap around and securely hold the folded body 12 in place or can be wrapped downward around the shoulder and arms of the baby and then tucked between the baby and the body 12. When the arms 14, 16 are folded in the latter manner, the length $L_1$ can be long enough to allow the ends of the arms 14, 16 to extend past the baby on the other side.

Each arm 14, 16 can have a width W. The width W can vary. The width W generally should be large enough to permit the covering of the shoulders of the baby when the arms 14, 16 of the wrap 10 are wrapped downwardly and diagonally over the shoulders of the baby.

Figure 20:
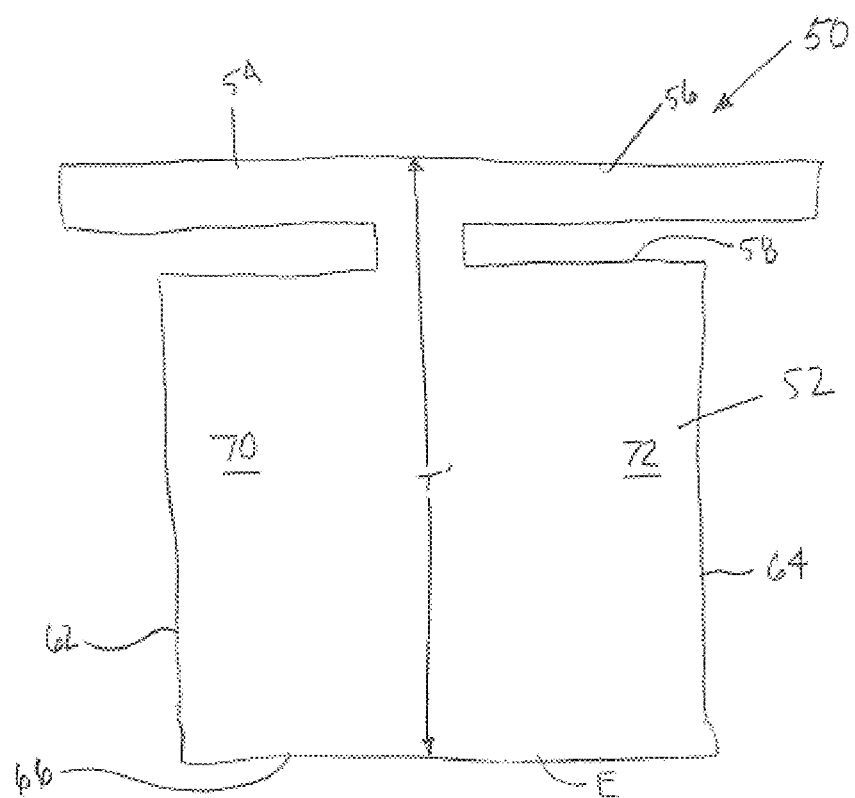
FIG. 20 illustrates a top perspective view of an embodiment of a wrap according to the present subject matter.

Alternatively, as shown in FIG. 20, a wrap 50 can have a body 52 that is be rectangular in shape with the arms 54, 56 extending outward and along a side 58. The side 58 can serve as a base of the rectangular-shaped body 52 in a similar manner to the arms 54, 56 in the wrap 50. The rectangular-shaped body 52 can have four sides 58, 62, 64, 66. The base side 58 of the body 52 can have the neck 60 extend therefrom. The side 66 opposite the base side 58 can form the end portion E of the body 52. The remaining sides 62, 64 of the body 52 can form peripheral side portions, or wings, 70, 72 configured to be folded across the body 52 and around a baby (not shown) placed on the body 52 in a similar manner as described with respect to wrap 10 above. The wrap 50 can have a width T'. The width T' can be measured from the sides of the arms 54, 56 distal from the body 52 to the end E of the body 52.

The width T' of wrap 50 with the rectangular shape can be a distance greater than a length of a baby being swaddled from the baby's torso to its feet such that the end portion E of the body 52 of the wrap extends past the baby's feet. Since the wrap 50 is rectangular, the wrapped peripheral side portions 70, 72 can serve as a blanket covering the baby's feet while still providing access to the baby's feet for attachment of a pulse oximeter, IV, or other medical devices to the legs or feet of the baby. Further, the access through the open end of the wrap 50 when wrapped around the baby can provide access to other parts of the baby's body allowing electrical or fluid lines through the opening while the baby is still wrapped and covered. The arms 54 and 56 can be wrapped around the baby in similar manners as will be described below to hold wrap 50 in place around the baby. Further, securement mechanisms can also be used to hold the arms around the wrap to secure the wrap 50 around the baby. Such securement mechanisms are also described below.

Figure 2:
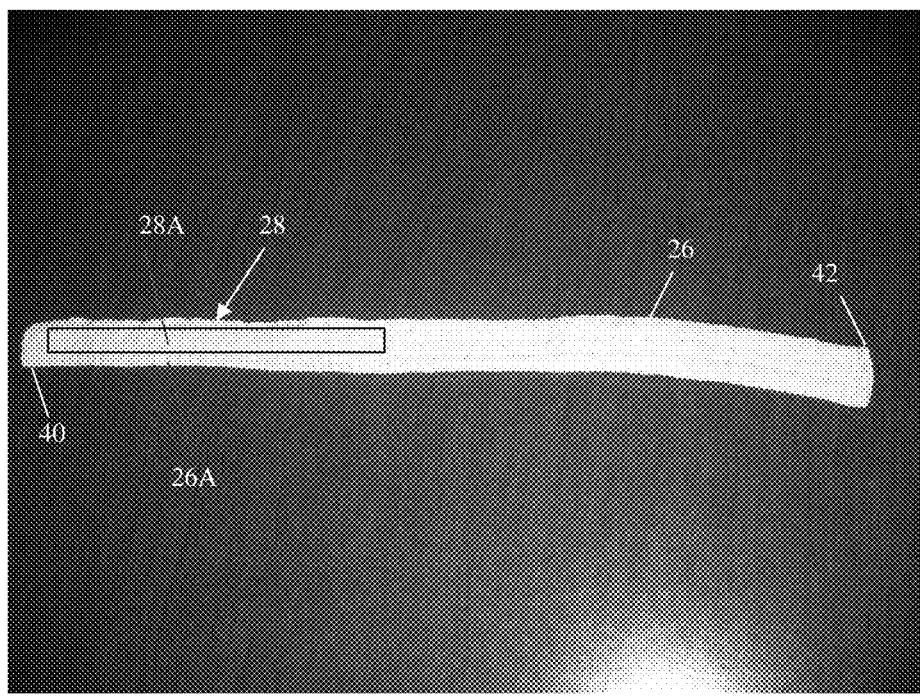
FIGS. 2 and 3 illustrate perspective views of an embodiment of a strap that can be use with the wrap according to FIG. 1.
Figure 3:
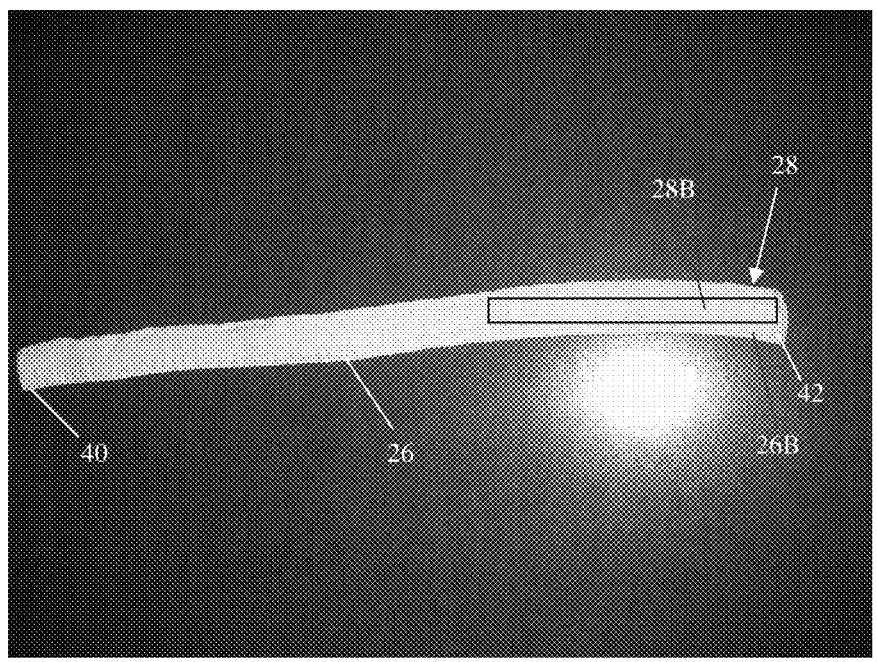

One such securement mechanism can be a strap 26 shown in FIGS. 1-3, 12, and 13. The strap 26 can be provided that can be placed around the wrap 10 once the wrap 10 is folded around a baby. As shown in FIGS. 2 and 3, the strap 26 can have a fastener mechanism generally designated 28 attached thereto to secure the wrap 10 in place. The fastener mechanism 28 can be snaps, magnets, adhesives, buttons, hook and loop fasteners, clasps, pins, buckles, or the like. For example, the strap 26 can have a hook and loop fastener 28 attached thereto, such as the hook and loop fasteners sold under the name VELCRO® by Velcro USA, Inc., of Manchester, N.H. The hook and loop fastener 28 can have a hook portion 28A on a first side 26A of a first end 40 of the strap 26 and a loop portion 28B on a second side 26B of a second end 42 of the strap 26. In this manner, when the strap 26 is wrapped around the folded wrap 10, the hook portion 28A will face the loop portion 28B to permit the ends 40, 42 to be secured together. The strap 26 can be separate from the body 12. Alternatively, the strap 26 can be attached to the back of the body 12. For example, the strap 26 can be attached through a fastener mechanism described above or can be permanently attached to the body 12.

Figure 21A:
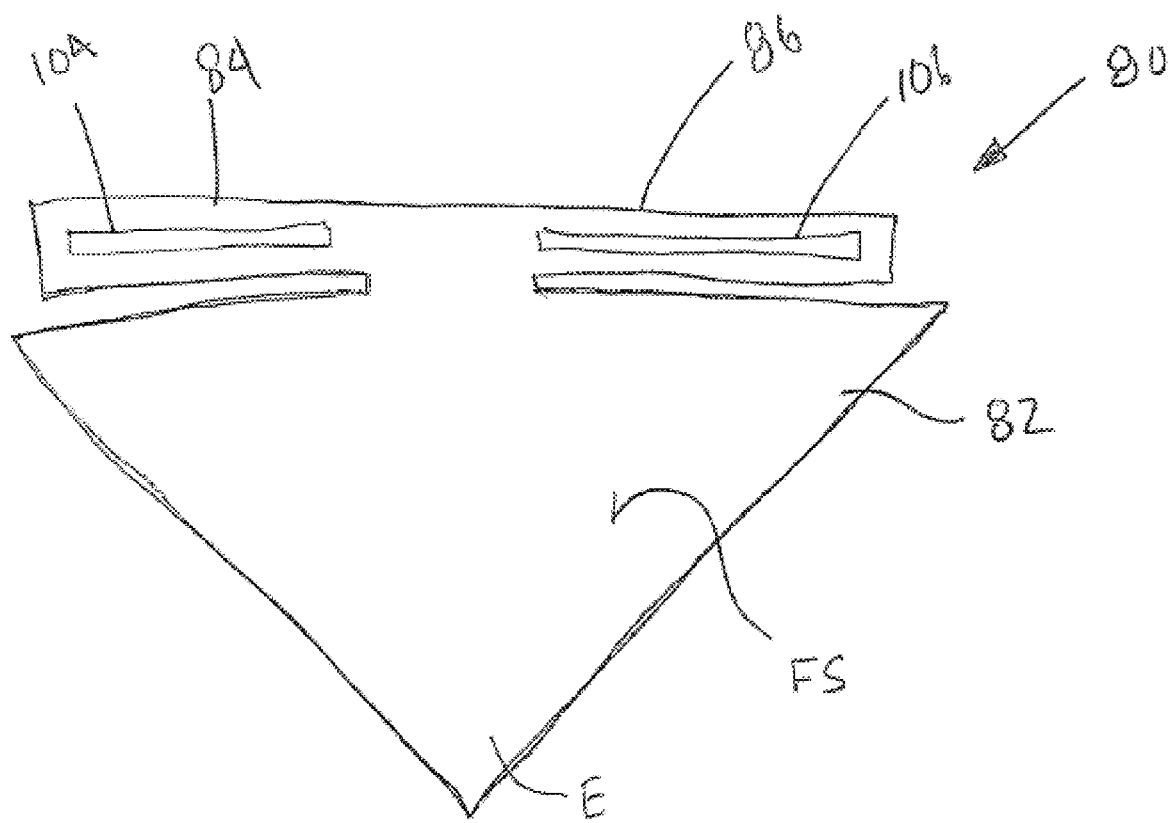
FIG. 21A illustrates a top perspective view of an embodiment of a wrap according to the present subject matter.
Figure 21B:
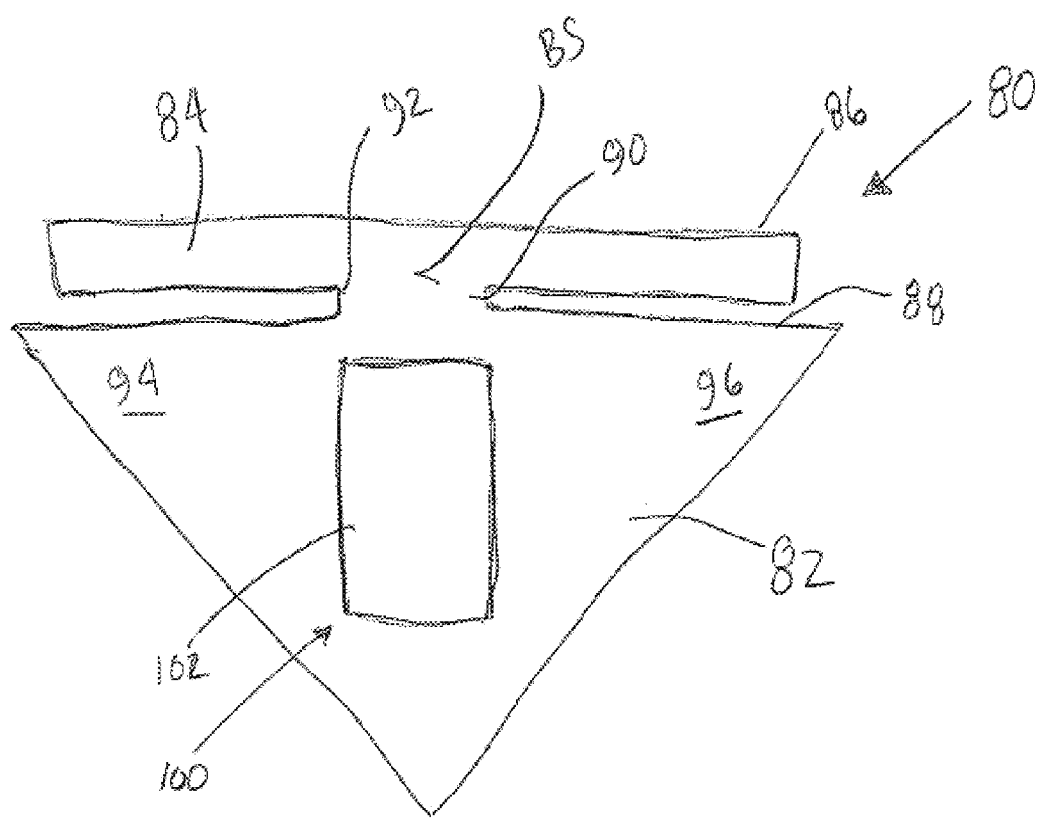
FIG. 21B illustrates a bottom perspective view of the embodiment of the wrap according to FIG. 21A.

Alternatively, other securement mechanisms can also be used, if desired. For example, a wrap, generally designated 80, can be used that includes securement mechanisms thereon as shown in FIGS. 21A and 21B. The wrap 80 is similar to the wrap 10 except that securement mechanisms 100 are secured thereon. The wrap 80 includes a body 82 with a first arm 84 and a second arm 86 attached to the body 82. The arms 84, 86 can generally extend along a side 88 of the body 82. The arms 84, 86 can extend about parallel to the side 88 of the body 82 along which they extend. The arms 84, 86 can reside against the side 88 of the body 82. Alternatively, the arms 84, 86 can be separated from the body 82. For example, a neck 90 can extend outward from the side 88 of the body 82. The neck 90 can serve as an attachment point for the arms 84, 86 to the body 82. The neck 90 can generally be centered along the side 88 of the body 82. The arms 84, 86 can extend outward from the end 92 of the neck 90 distal from the side 88 of the body 82.

Figure 21C:
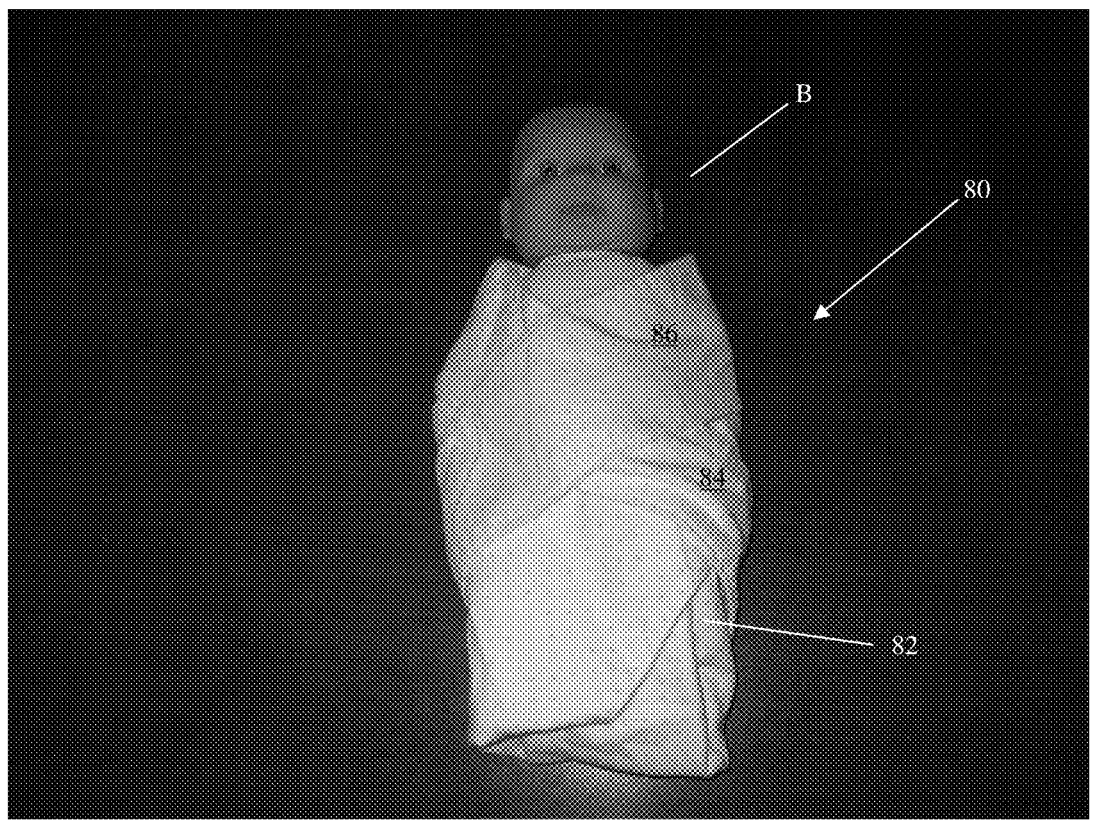
FIG. 21C illustrates a perspective view of the embodiment of the wrap according to FIG. 21A wrapped around a baby.

Securement mechanisms 100 can be positioned on a front side FS of the wrap 80 as shown in FIG. 21A and on a backside BS as shown in FIG. 21B. The securement mechanisms 100 can be fasteners that can engage each other to hold the wrap 80 in place. For example, the securement mechanism can be a hook and loop fastener as shown in the embodiment in FIGS. 21A-21C. As shown in FIG. 21A, hook portions 104 and 106 can be secured to the arms 84, 86 on the front side FS of the wrap 80. As shown in FIG. 21B, a loop portion 102 can be secured to the body 82 on the back side BS of the wrap 80. When wrap 80 is properly wrapped around a baby B as shown in FIG. 21C, segments of the hook portions 104, 106 of the arms 84, 86 can engage areas of the loop portion 102 of the body 82. The engagements between the hook portions 104, 106 and the loop portion 102 hold the arms in place over the shoulders of the baby and around the body 82 of the wrap 80 to secure the wrap around the baby B as shown in FIG. 21C.

The peripheral side portions 94, 96 can be wrapped at least partially around a baby that is placed in the middle of the wrap 80. The end portion E of the body 82 can be folded up as with swaddling blankets or left unfolded. The arms 84, 86 can be wrapped downward in a diagonal direction around the folded peripheral side portions 94, 96 so that the arms 84, 86 wrap around and securely hold the folded body 82 in place. When the arms 84, 86 of the wrap 80 are wrapped downwardly and diagonally over the shoulders of the baby, the shoulders of the baby are covered and the baby is held in place within the wrap 80. When the arm 84 is folded, a segment of hook portion 104 of the arm 84 can contact an area of the loop portion 102 on body 82 and back side BS of wrap 80. When the arm 86 is folded, a segment of hook portion 106 of the arm 86 can also contact an area of the loop portion 102 on body 82 and back side BS of wrap 80. With the hook portions 104, 106 of the arms 84, 86 engaging areas of the loop portion 102 of the body 82, the wrap 80 can be secured around the baby as shown in FIG. 21C. The strips of the hook portions 104, 106 can be long enough and the area covered by the loop portion can be large enough so that the wrap 80 can accommodate babies of different sizes.

Figure 4:
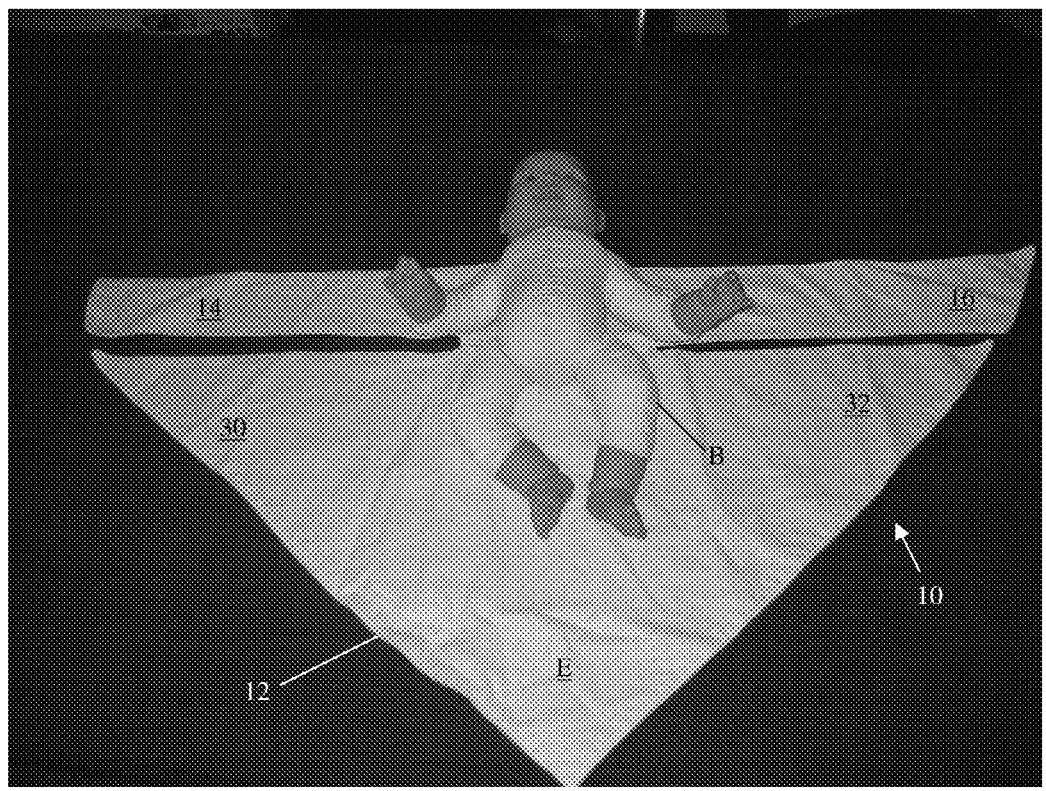
FIGS. 4-13 illustrate perspective views of possible steps for an embodiment of a method of use of the wrap according to FIG. 1.
Figure 5:
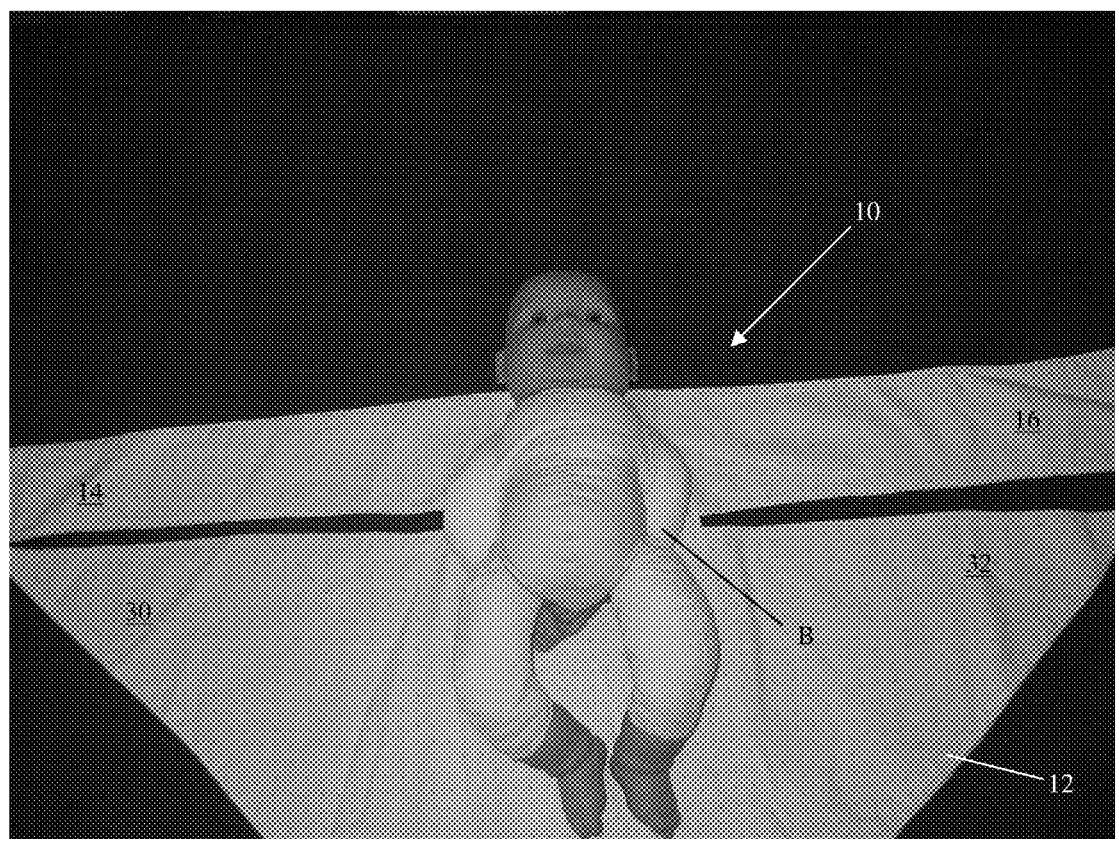

An example of a method of use of the wrap 10 is illustrated in FIGS. 4-13. In use, the wrap 10 can be laid flat as shown in FIG. 4. A baby B can be placed in the middle of the wrap 10 along the axis A with the head of the baby B extending above the arms 14, 16. The shoulders of the baby B can reside within at least one of the neck 20 or the arms 14, 16. Optionally, depending on the use of the wrap 10, the arms of the baby B can be placed behind its back as shown in FIG. 5. Such a position can be useful for procedures like echocardiograms where an unobstructed chest is necessary for performing the procedures.

Figure 6:
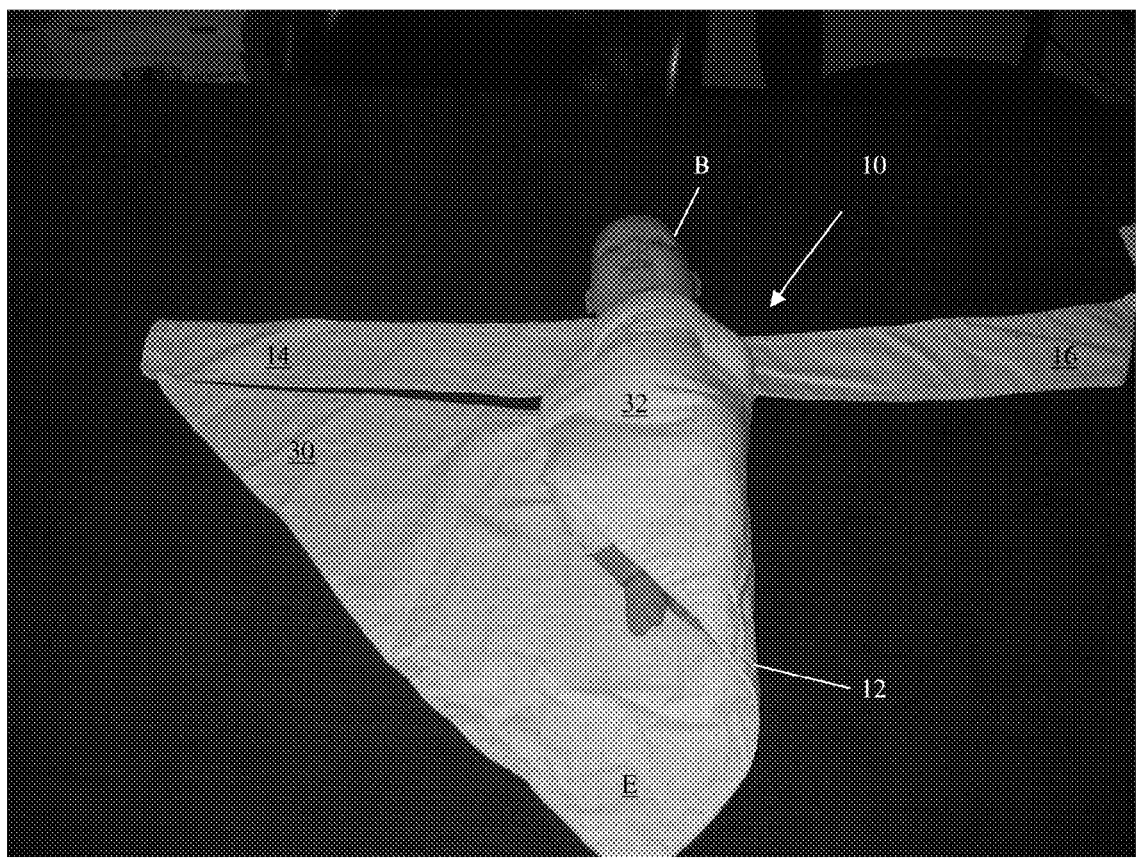
Figure 7:
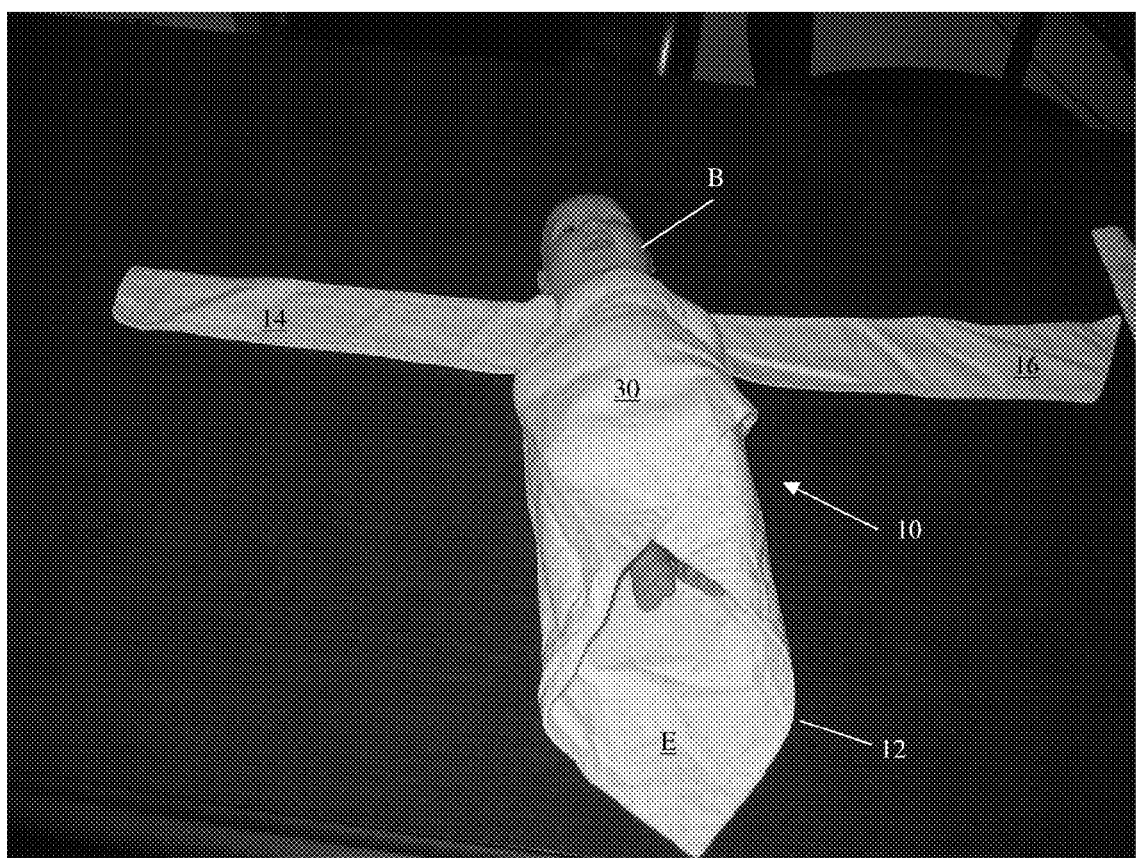

At this point, one of the peripheral side portions 30, 32 can be folded around the baby B. Either peripheral side portion 30, 32 can be folded first with the other peripheral side portion being folded second. For example, a first peripheral side portion 32 can be folded around and tucked under the baby B as shown in FIG. 6. As can be seen, the shoulders of the baby can reside outside the wrapped portion at this point. The second peripheral side portion 30, can be folded snugly around the baby B as shown in FIG. 7.

Figure 8:
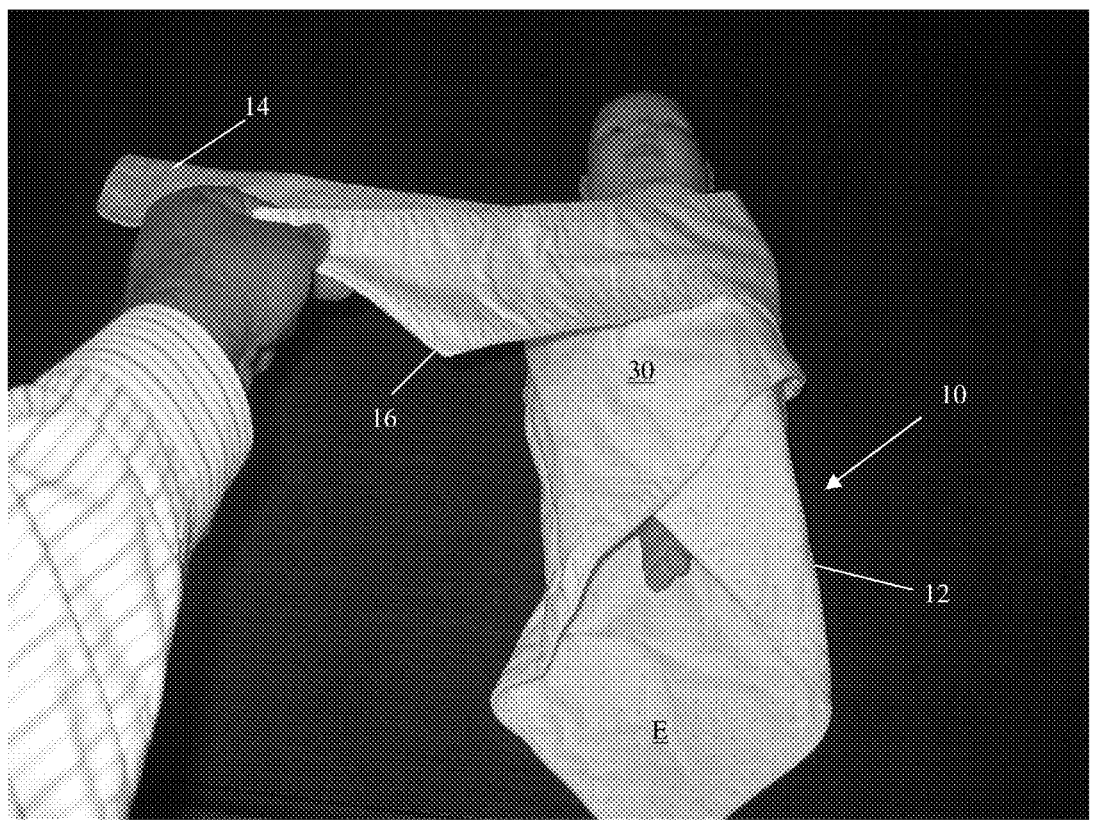
Figure 9:
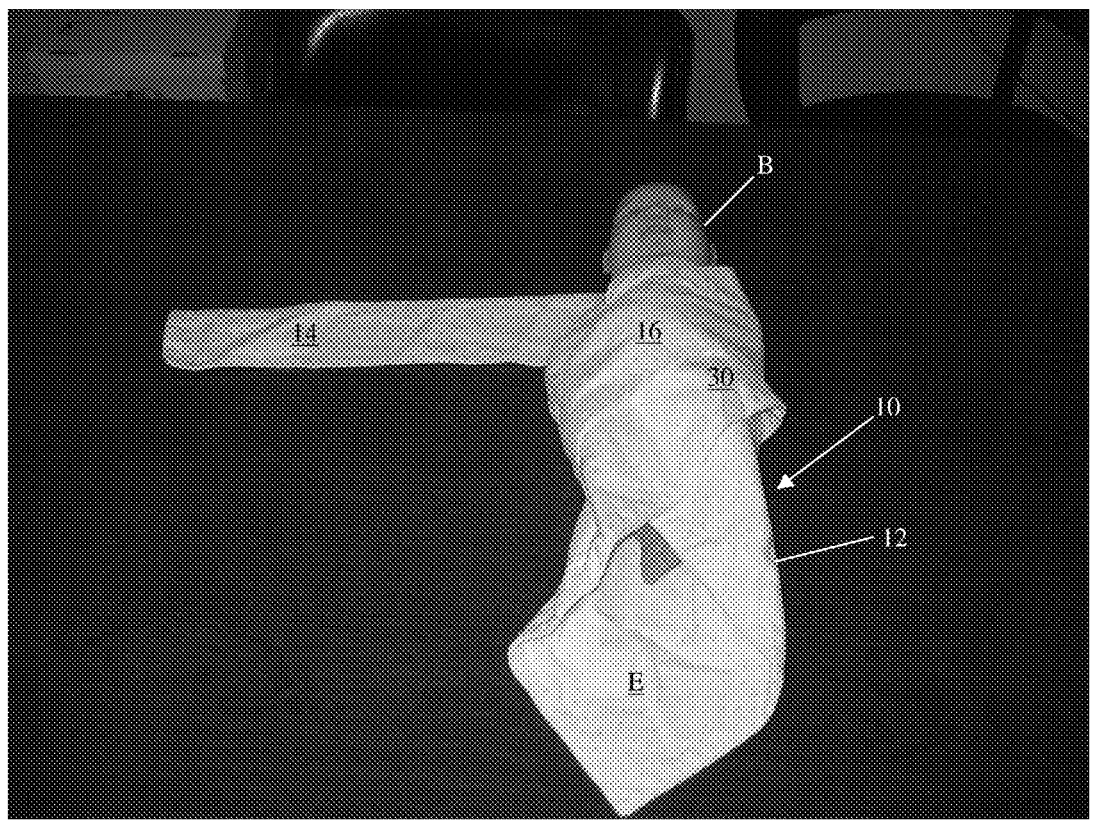
Figure 10:
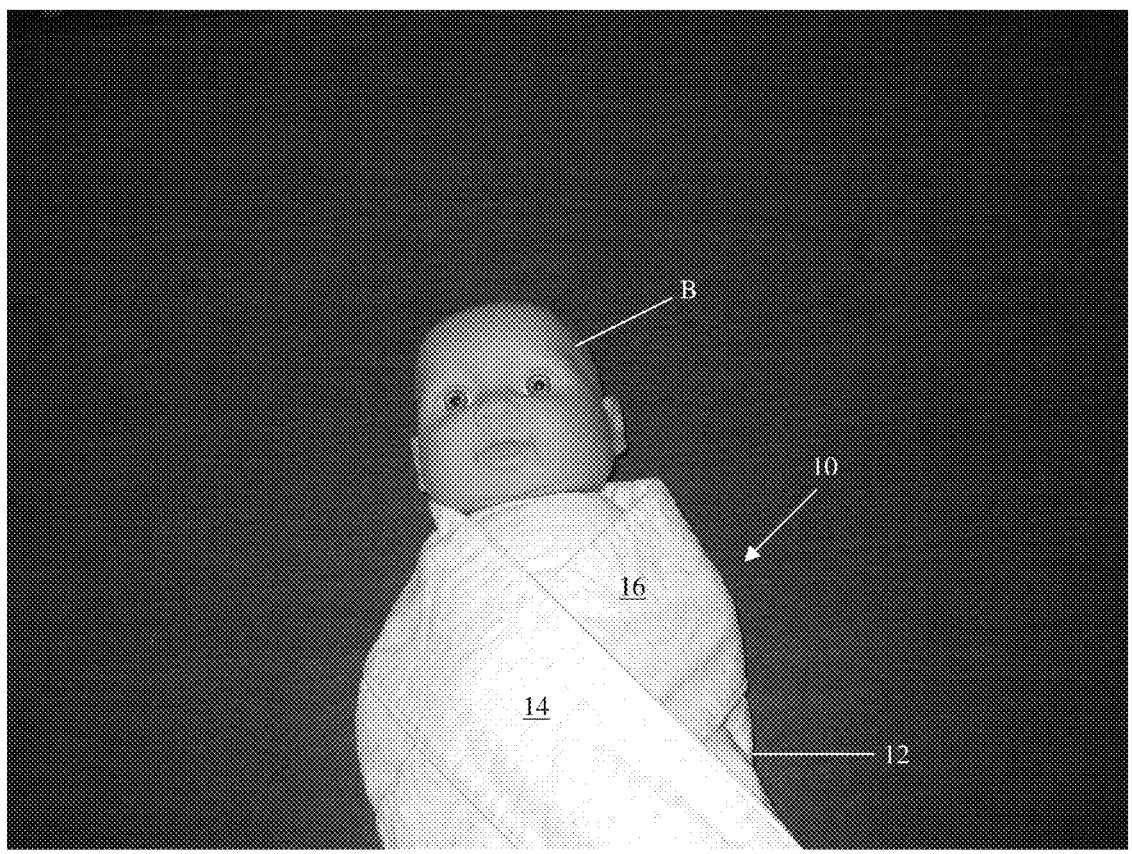
Figure 11:
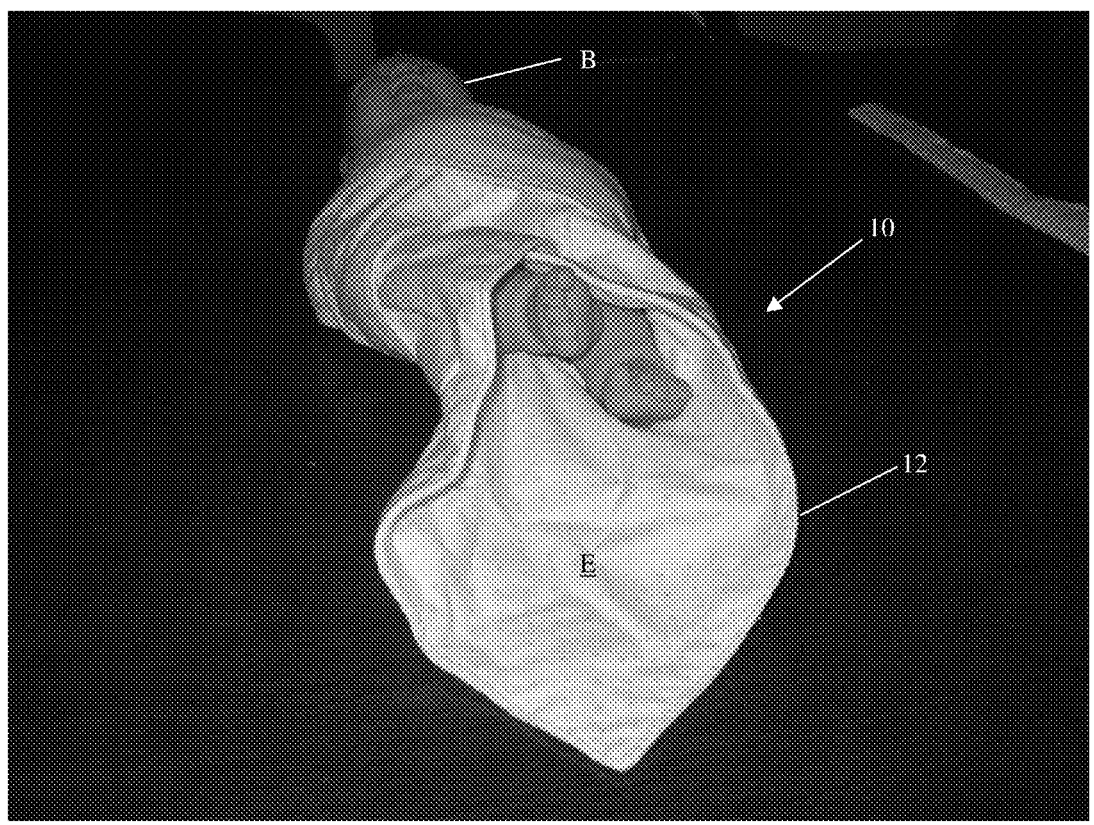

In FIG. 8, arm 16 can be folded diagonally and downward over the shoulder of the baby B. The end of the arm 16 can be folded so that the arm 16 wraps across, down and around the body of the baby B with the arm 16 tuck behind the baby B as shown in FIG. 9. In FIG. 10, arm 14 can be folded diagonally and downward over the shoulder of the baby B. The end of the arm 14 can be folded so that the arm 14 wraps across, down and around the body of the baby B and over arm 16 with the arm 14 tuck behind the baby B. Either arm 14, 16 can be folded first with the other arm being folded second. In this manner, with the downward diagonally folded arms 14, 16, the baby B is held tightly in the wrap 10 with the arms and shoulders at least partially immobilized. The downward and diagonal folds of the arms 14, 16 can provide extra holding force that a conventional swaddling blanket does not provide. When placing the baby B on the wrap 10, the head can be above the top portion of the arms 14, 16 and neck 20 distal from the body 12, while the shoulders can be below this top portion. Such placement of the baby B facilitates the immobilization of the shoulders and arms of the baby B after folding the arms 14, 16 and peripheral side portions 30, 32 of the wrap 10.

The configuration of the wrap 10 is also conducive for chest procedures, because the body 12 of the wrap 10 is positioned well below the shoulders of the baby B. In such an embodiment, the wrapping of the peripheral side portions 30, 32 only covers the mid to lower torso of the baby B. Only the arms 14, 16 of the wrap 10 cover the shoulder and chest region of the baby B. Alternatively, the arms 14, 16 of the wrap 10 can be wrapped over the shoulder and arms of the baby B and are then placed behind the baby's back, leaving the chest region of the baby B exposed as will be described in more detail below. Depending on the angle of the downward diagonal folds of the arms 14, 16, the chest region of the baby B can be left at least partially exposed.

As can be seen in FIGS. 7-9, and 11, with the wrap 10 folded in the manner described above, the end portion E of the body 12 distal from the arm 14, 16 can be left unfolded to allow access to the feet of the baby. This permits attachment of a medical device, such as a pulse oximeter, to the toes of the feet of the baby B.

Figure 12:
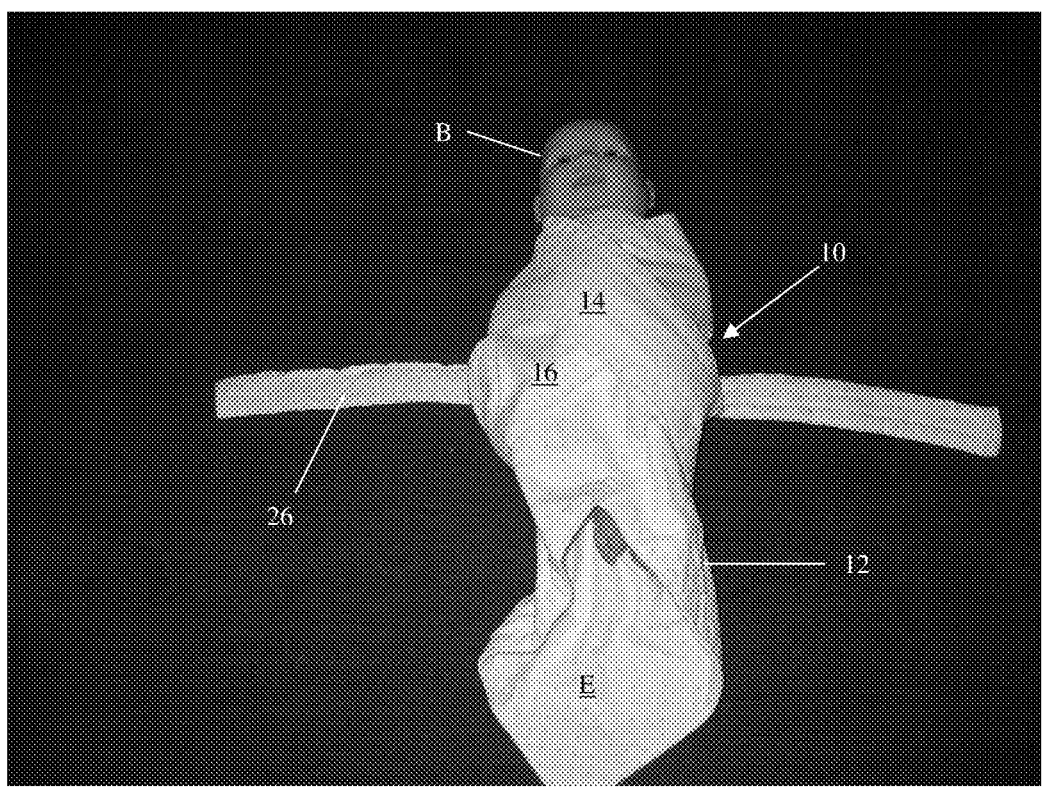
Figure 13:
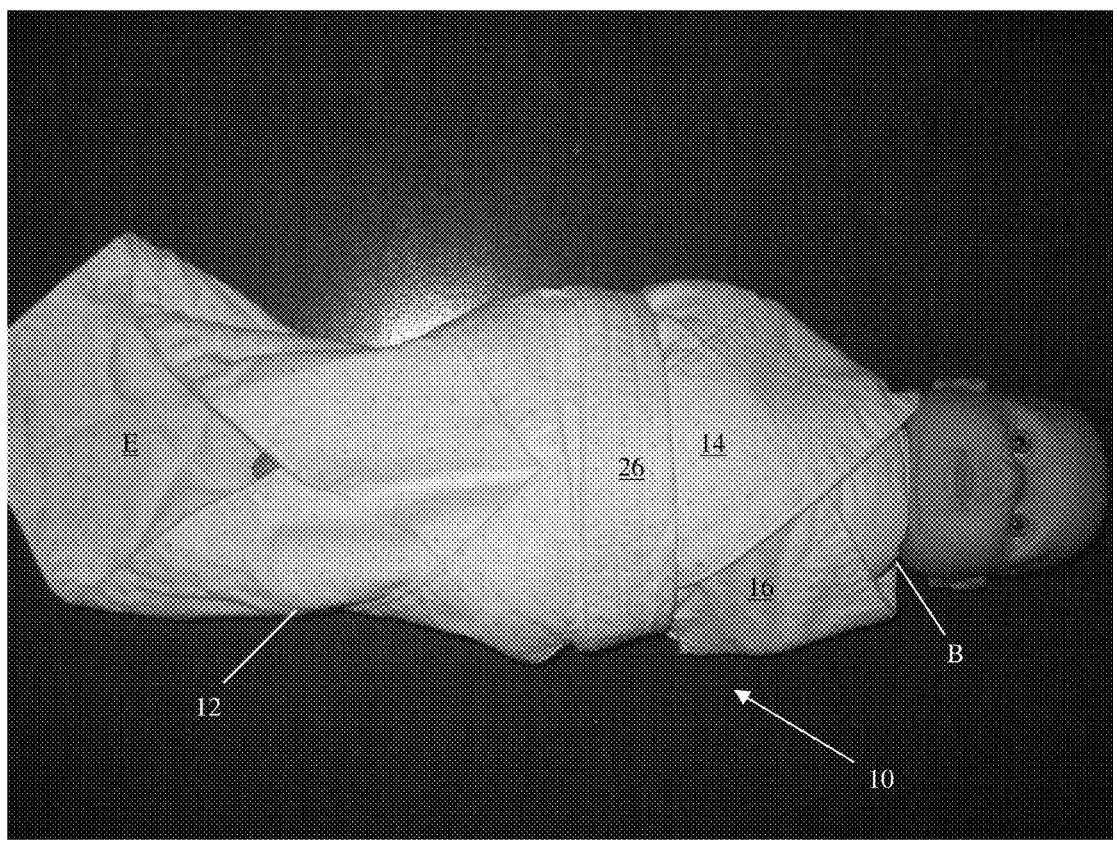

As shown in FIGS. 12 and 13, a strap can optionally be wrapped around the baby B and wrap 10. The strap 26 can be put under the wrapped baby B. A first end 26A can be pulled around the baby B to the front of the baby B so that a first portion of the fastener 28 is exposed. The second end 26B can then be pulled around the baby B so that the second portion of the fastener 28 faces and attaches to the first portion of the fastener 28.

Figure 14:
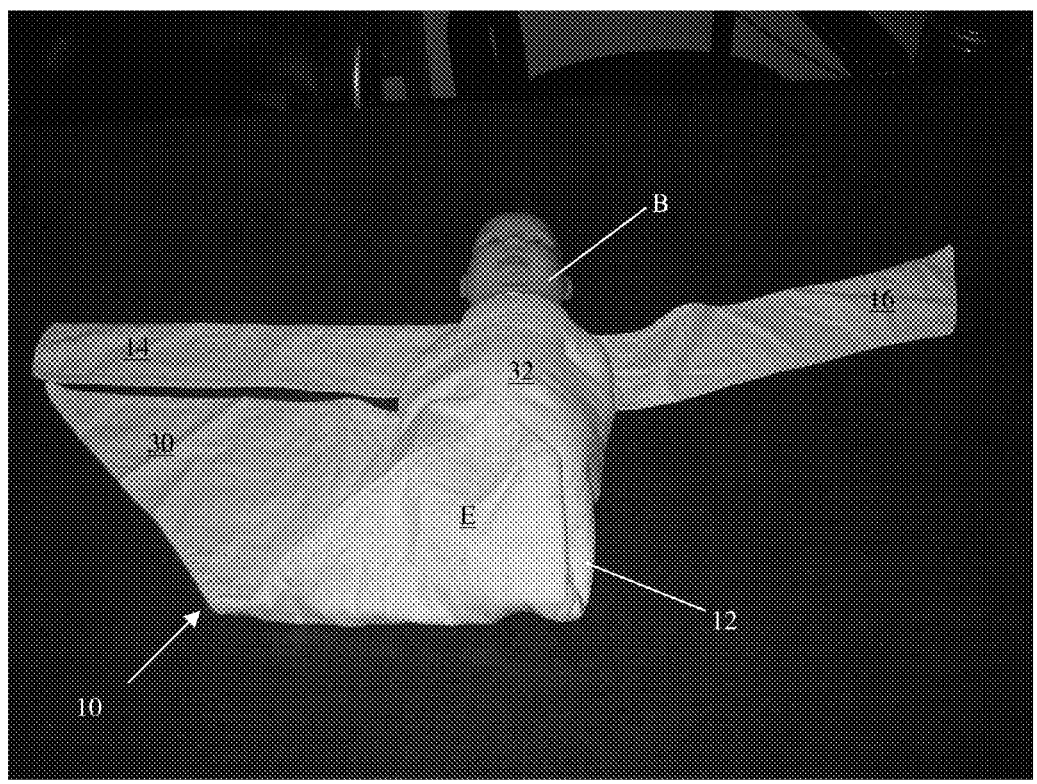
FIGS. 14-19 illustrate perspective views of possible steps for another embodiment of a method of use of the wrap according to FIG. 1.
Figure 15:
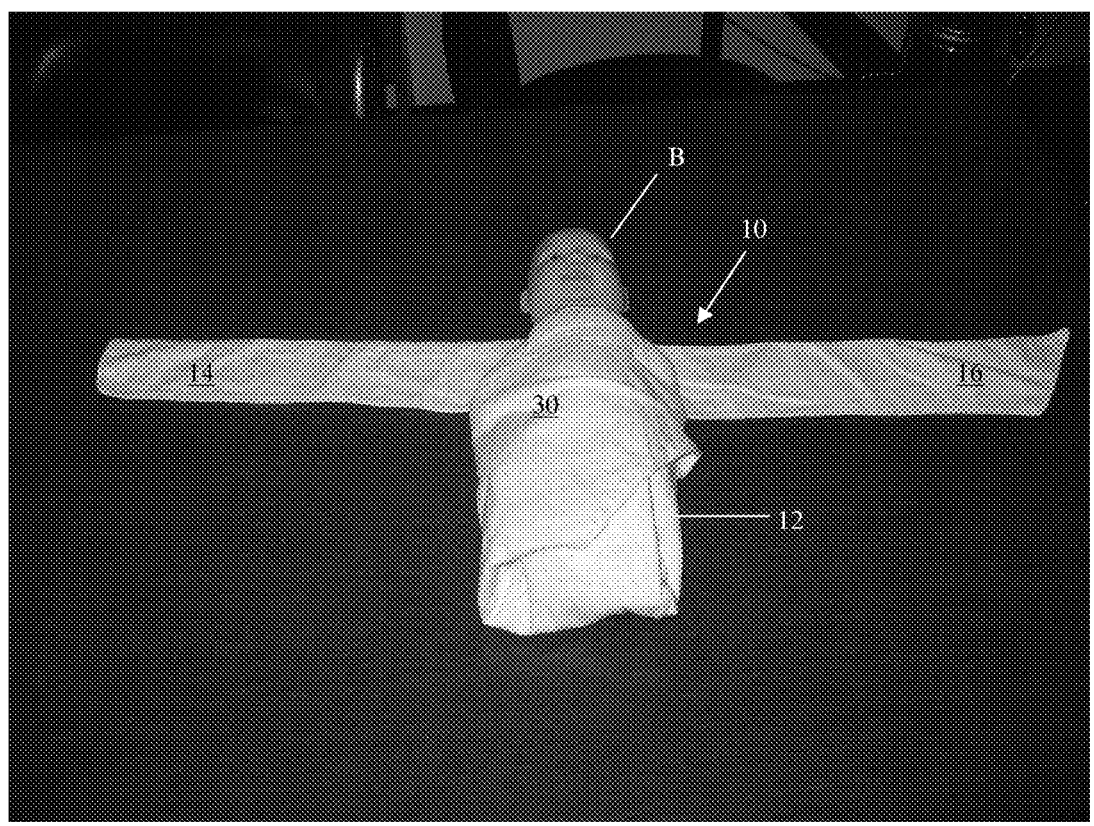

As shown in FIGS. 14-19, a second method of folding the wrap 10 about a baby B is provided. The folding in this method is similar to the method described above except that the end portion E is folded upward toward the body 12 of the wrap 10 and the body of the baby B after the folding of a first peripheral side portion 32 as shown in FIG. 14. The second peripheral side portion 30 can then be folded as shown in FIG. 15.

Figure 16:
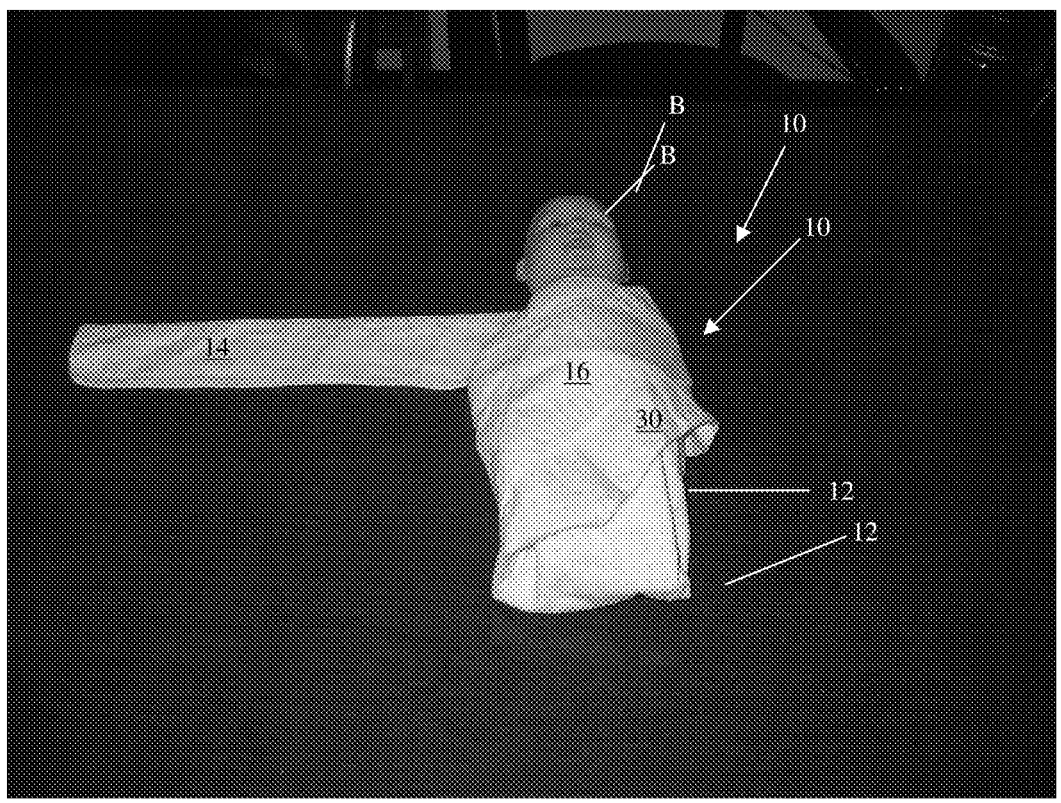

The arm 16 can be folded diagonally and downward over the shoulder of the baby B. The end of the arm 16 can be folded so that the arm 16 wraps across, down and around the body of the baby B with the arm 16 tuck behind the baby B as shown in FIG. 16. The arm 14 can be folded diagonally and downward over the shoulder of the baby B. The end of the arm 14 can be folded so that the arm 14 wraps across, down and around the body of the baby B and over arm 16 with the arm 14 tuck behind the baby B.

Figure 17:
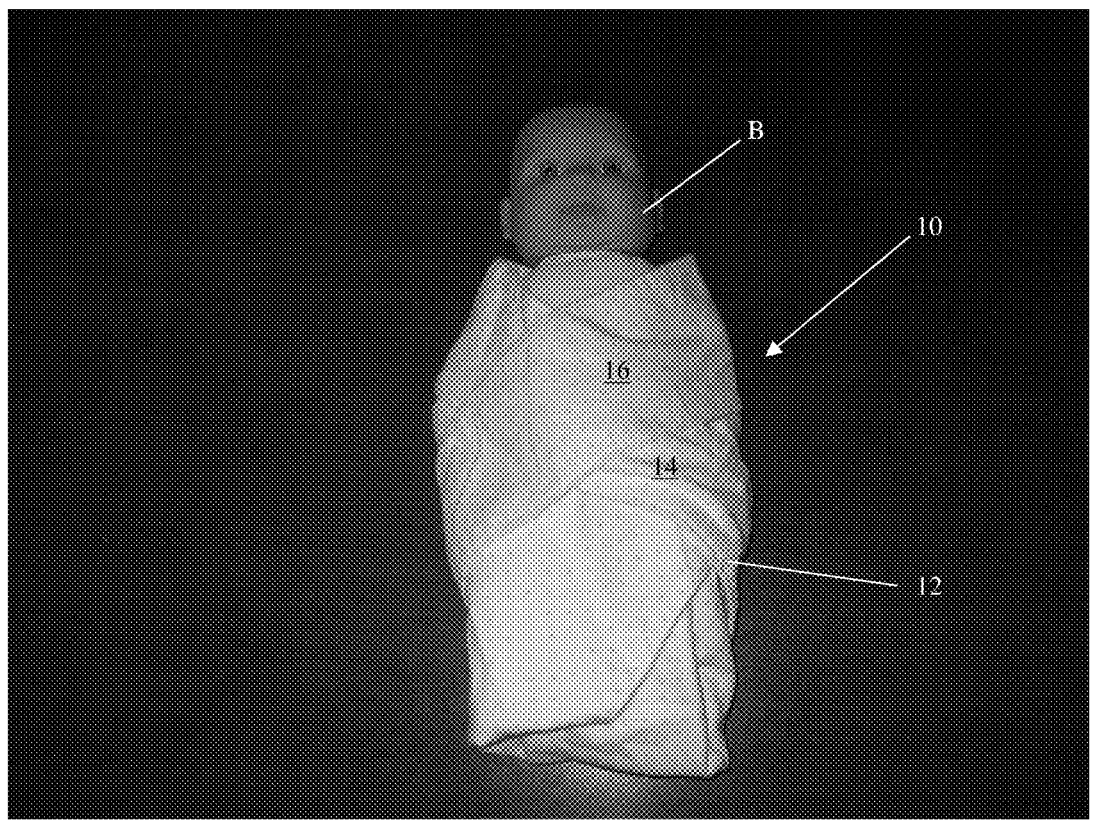

Alternatively, as shown in FIG. 17, the arm 14 can be folded diagonally and downward over the shoulder and tucked behind the baby B first and then the arm 16 can be folded diagonally and downward over the shoulder and tucked behind of the baby B. In this manner, with the downward diagonally folded arms 14, 16, the baby B is held tightly in the wrap 10 with the arms and shoulders of the baby at least partially immobilized. The downward and diagonal folds of the arms 14, 16 can provide extra holding force that a conventional swaddling blanket does not provide.

Figure 18:
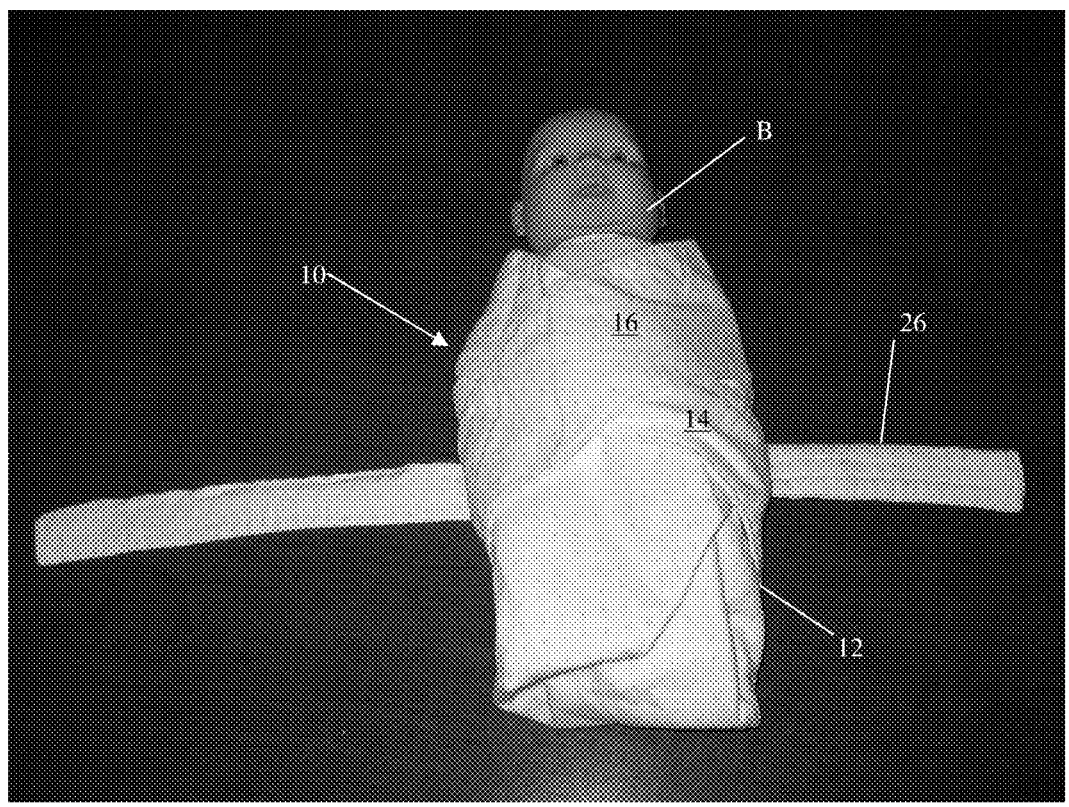
Figure 19:
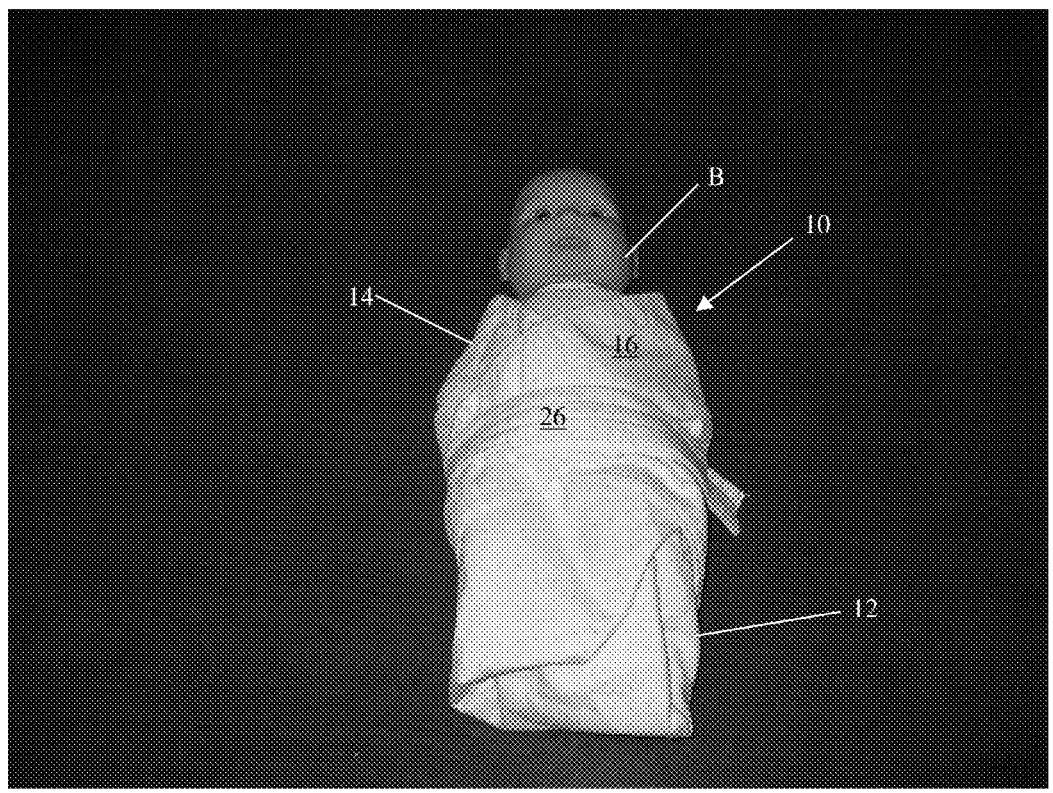

As shown in FIGS. 18 and 19, a strap 26 can be wrapped around the baby B and wrap 10. The strap 26 can be put under the wrapped baby B. A first end 26A can be pulled around the baby B to the front of the baby B so that a first portion of the fastener 28 is exposed. The second end 26B can then be pulled around the baby B so that the second portion of the fastener 28 faces and attaches to the first portion of the fastener 28 as shown in FIG. 19.

Figure 22:
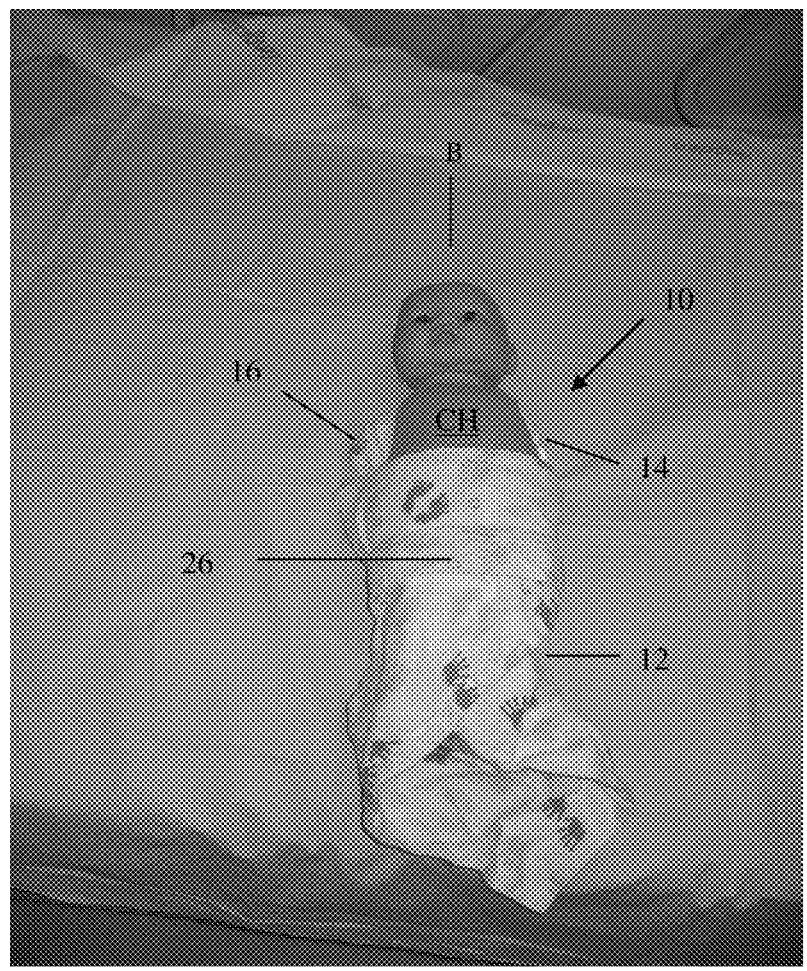
FIGS. 22-31 illustrate perspective views of possible steps for another embodiment of a method of use of the wrap according to FIG. 1.

Another example of a method of use of the wrap 10 is illustrated in FIGS. 22-31. For example, this method can be used in conjunction with medical procedures such as echocardiograms, upper G.I. procedures, or the like, where the chest region is needed to be exposed. As shown in FIG. 22, the baby B is wrapped with her arms $AR_L$, $AR_R$ behind her back and/or bound by the arms 14, 16 of the wrap 10 with her chest region CH exposed. The arms 14, 16 of the wrap 10 are wrapped over the shoulder and arms $AR_L$, $AR_R$ of the baby B and are then placed behind the baby's back, leaving the chest region CH of the baby B exposed. The peripheral side portions 30, 32 are folded over the lower torso and/or legs of the baby B and the strap 26 is wrapped around the folded peripheral side portions 30, 32 to further hold the wrap in place.

Figure 23:
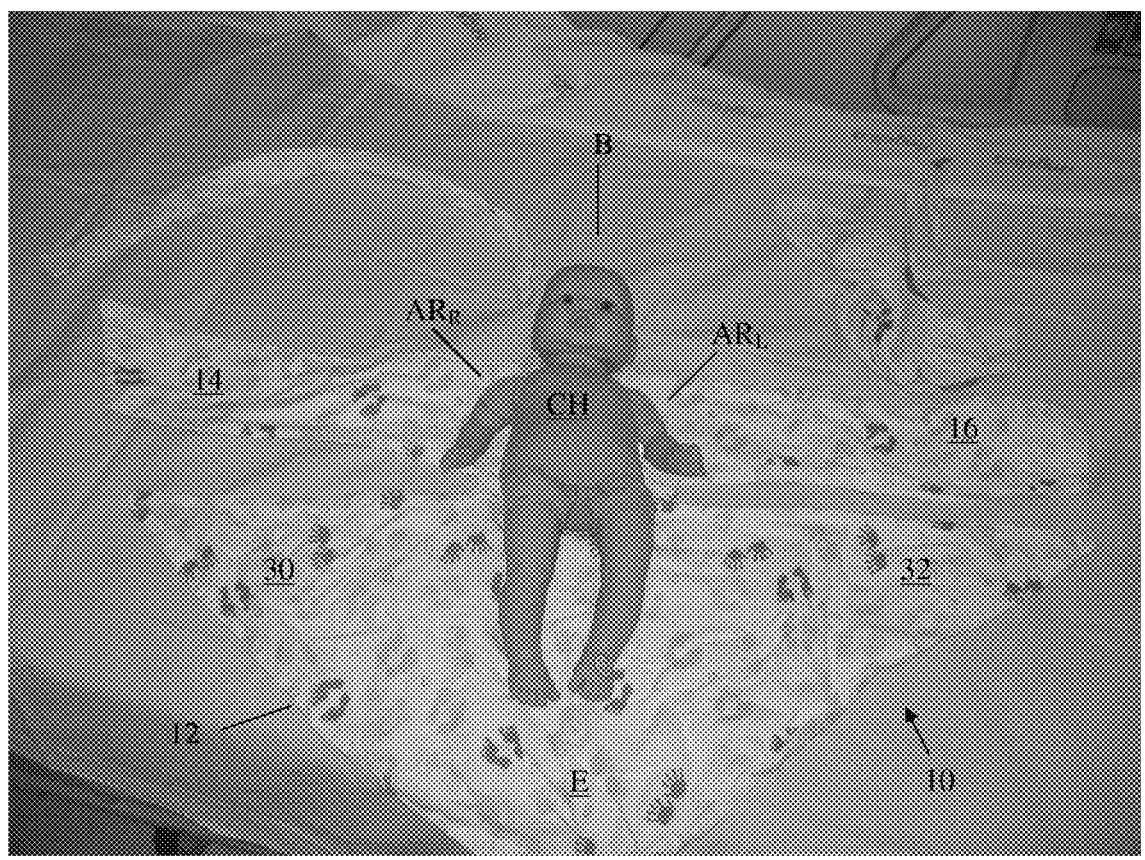

In use, the wrap 10 can be laid flat as shown in FIG. 23. A baby B can be placed in the middle of the wrap 10 along the axis A with the head of the baby B extending above the arms 14, 16. The shoulders of the baby B can reside within at least one of the neck 20 or the arms 14, 16. The arms $AR_L$, $AR_R$ of the baby B can be placed behind its back or held to its side by the folding of the wrap 10. Such a position can be useful for procedures like echocardiograms where an unobstructed chest is necessary for performing the procedures. When placing the baby B on the wrap 10, the head can be above the top portion of the arms 14, 16 and neck 20 distal from the body 12, while the shoulders can be below this top portion. Such placement of the baby B facilitates the immobilization of the shoulders and arms of the baby B after folding the arms 14, 16 and peripheral side portions 30, 32 of the wrap 10.

Figure 24:
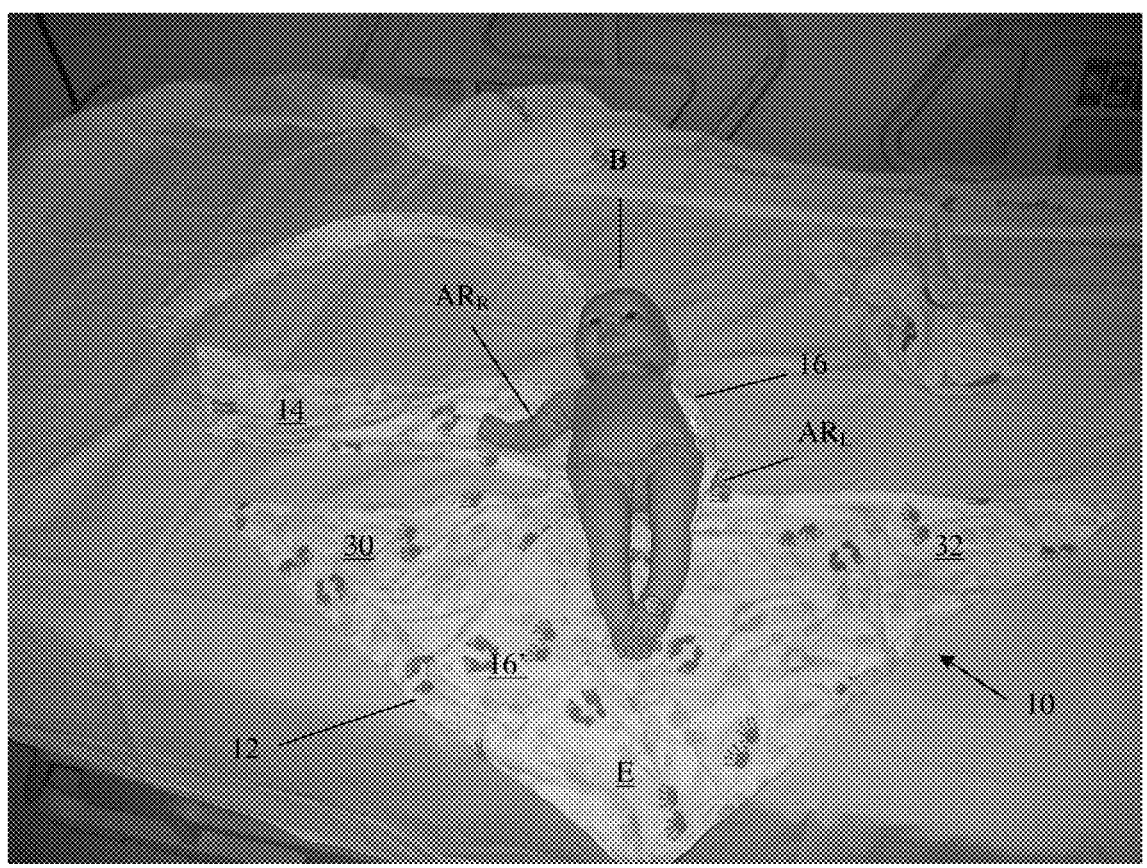
Figure 25:
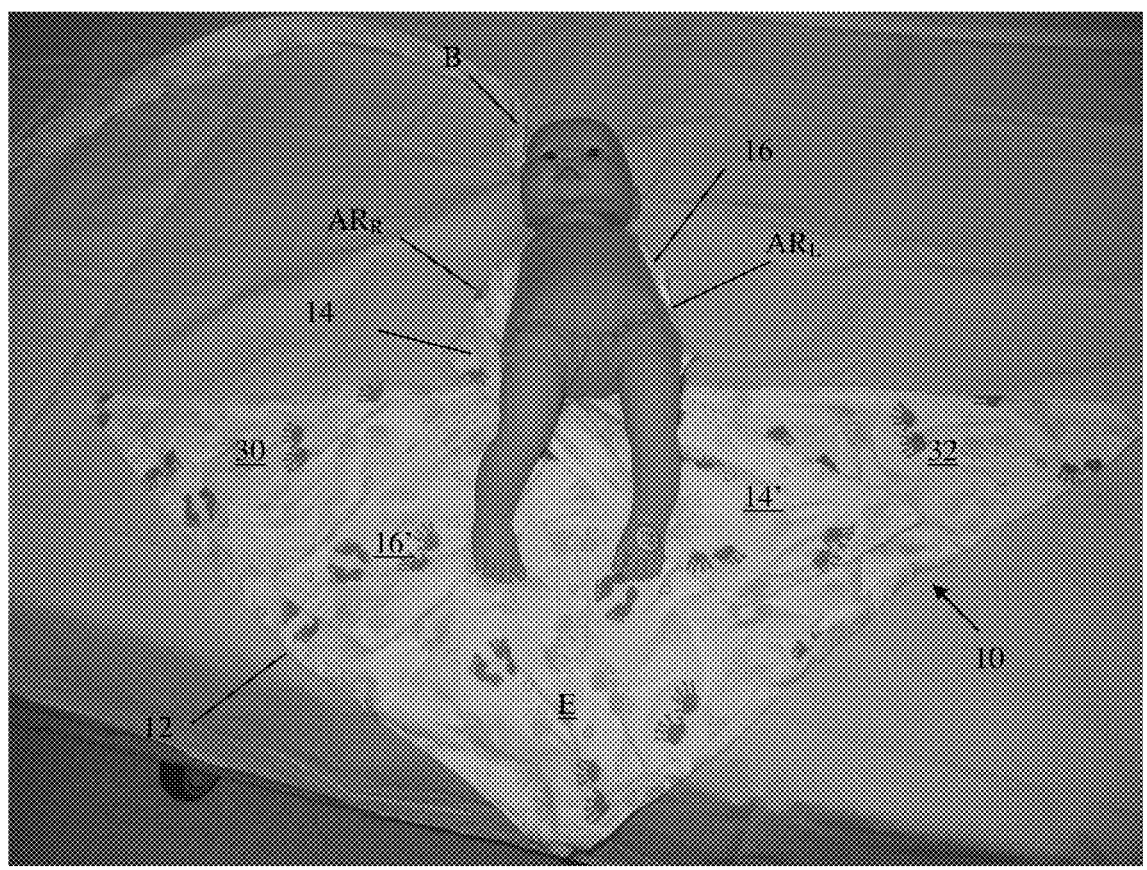

As shown in FIG. 24, the arm 16 of the wrap 10 can be folded diagonally and downward over the shoulder of the baby B and over the arm $AR_L$. For example, the arm 16 of the wrap 10 can be folded around the arm $AR_L$. The arm 16 of the wrap 10 can then be placed behind the body of the baby B. The arm 16 of the wrap 10 can reside between the body 12 of the wrap 10 and the body of the baby B with the end 16' of the arm 16 of the wrap 10 extending past the body of the baby B. In FIG. 25, the arm 14 of the wrap 10 can be folded diagonally and downward over the shoulder of the baby B and over the arm $AR_R$. For example, the arm 14 of the wrap 10 can be folded around the arm $AR_R$. The arm 14 of the wrap 10 can then also be placed behind the body of the baby B. The arm 14 of the wrap 10 can reside between the body 12 of the wrap 10 and the body of the baby B with the end 14' of the arm 14 of the wrap 10 extending past the body of the baby B. Either arm 14, 16 can be folded first with the other arm being folded second.

Figure 26:

With the arms 14, 16 folded in this manner, the baby B is held tightly in the wrap 10 with the arms $AR_L$, $AR_R$ and shoulders of the baby at least partially immobilized while the chest region CH of the baby B is left exposed. In particular, with the folded arms 14, 16 wrapped over and around the shoulder and arms $AR_L$, $AR_R$ of the baby B, the arms $AR_L$, $AR_R$ are held either behind the body of the baby B or beside the body of the baby B. To increase the immobility of the baby's arms $AR_L$, $AR_R$, the ends 14', 16' of the folded arms 14, 16 can be pulled in a direction away from the baby B to snugly tighten the arms 14, 16 of the wrap 10 around shoulder and arms $AR_L$, $AR_R$ of the baby B as shown in FIG. 26.

Figure 27:
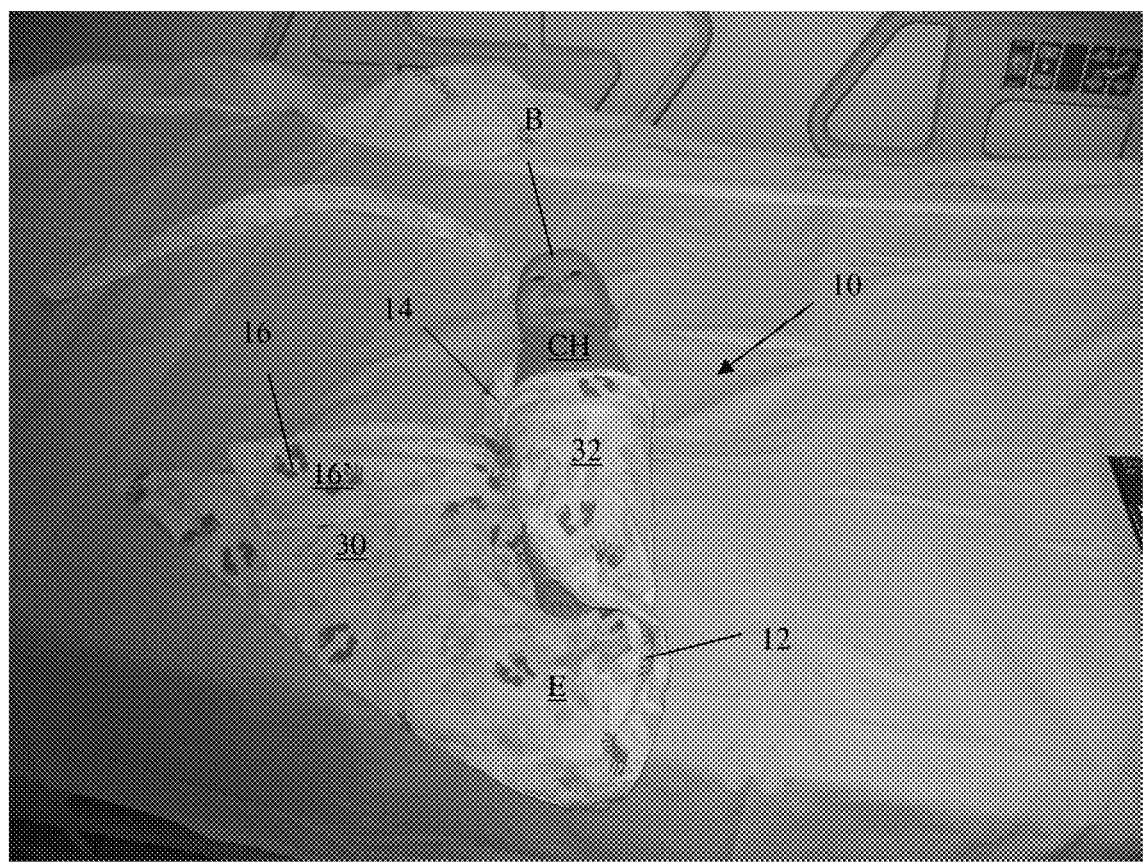
Figure 28:
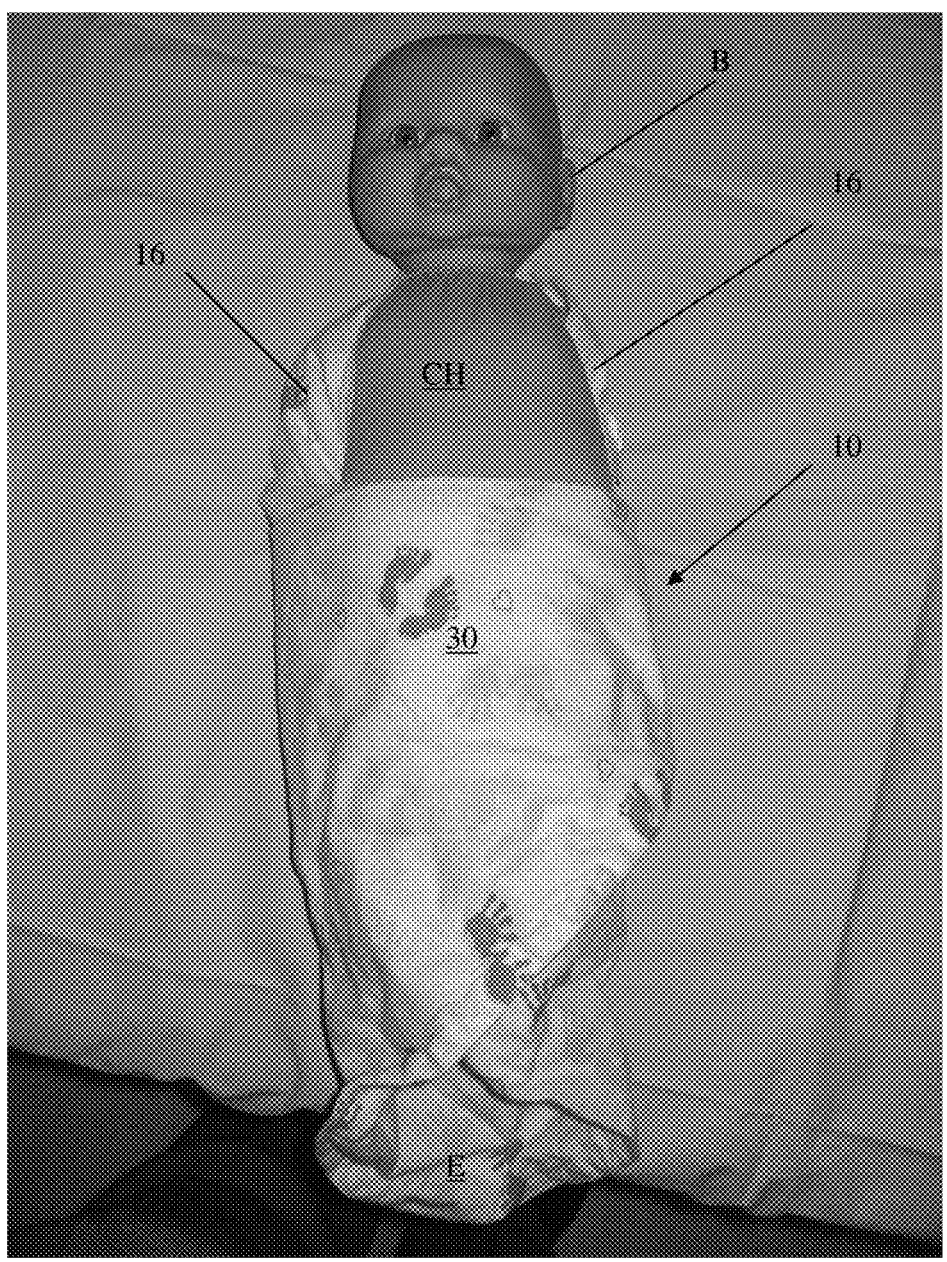

At this point, one of the peripheral side portions 30, 32 can be folded around the legs and/or lower torso of the baby B, leaving the chest region CH of the baby B exposed. Either peripheral side portion 30, 32 can be folded first with the other peripheral side portion being folded second. For example, a first peripheral side portion 32 can be folded around and tucked under the baby B as shown in FIG. 27. As can be seen, the shoulders of the baby can reside outside the wrapped portion at this point. The second peripheral side portion 30 can be folded around the first peripheral side portion 32 and the baby B as shown in FIG. 28. Both peripheral side portions 30, 32 can be folded snugly to a point of decreased mobility of the legs of the baby B. When folding the peripheral side portions 30, 32, the ends of the arms 14, 16 can be folded with the peripheral side portions 30, 32 over the top of the baby B, thereby further securing the wrap 10 and particularly the arms 14, 16 of the wrap 10 in place while leaving the chest region CH of the baby B exposed.

Figure 29:

As can be seen in FIG. 29, with the wrap 10 folded in the manner described above, the end portion E of the body 12 distal from the arm 14, 16 can be left unfolded to allow access to the body BO of the baby B. For example, access is easily provided to the feet F of the baby B This access permits attachment of medical devices, such as a pulse oximeter, to the body BO of the baby B, for example, the toes of the feet F of the baby B.

Figure 30:
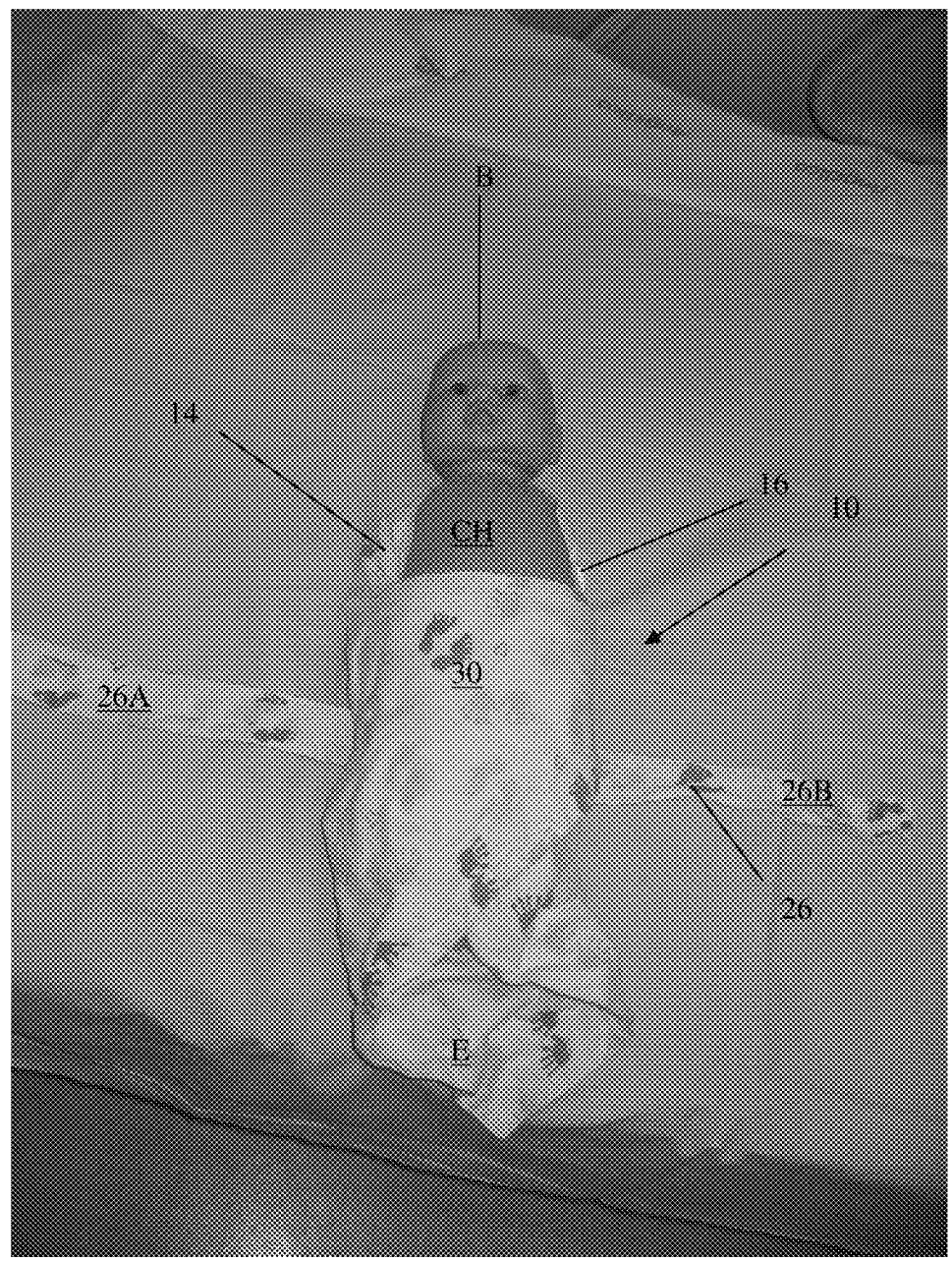
Figure 31:
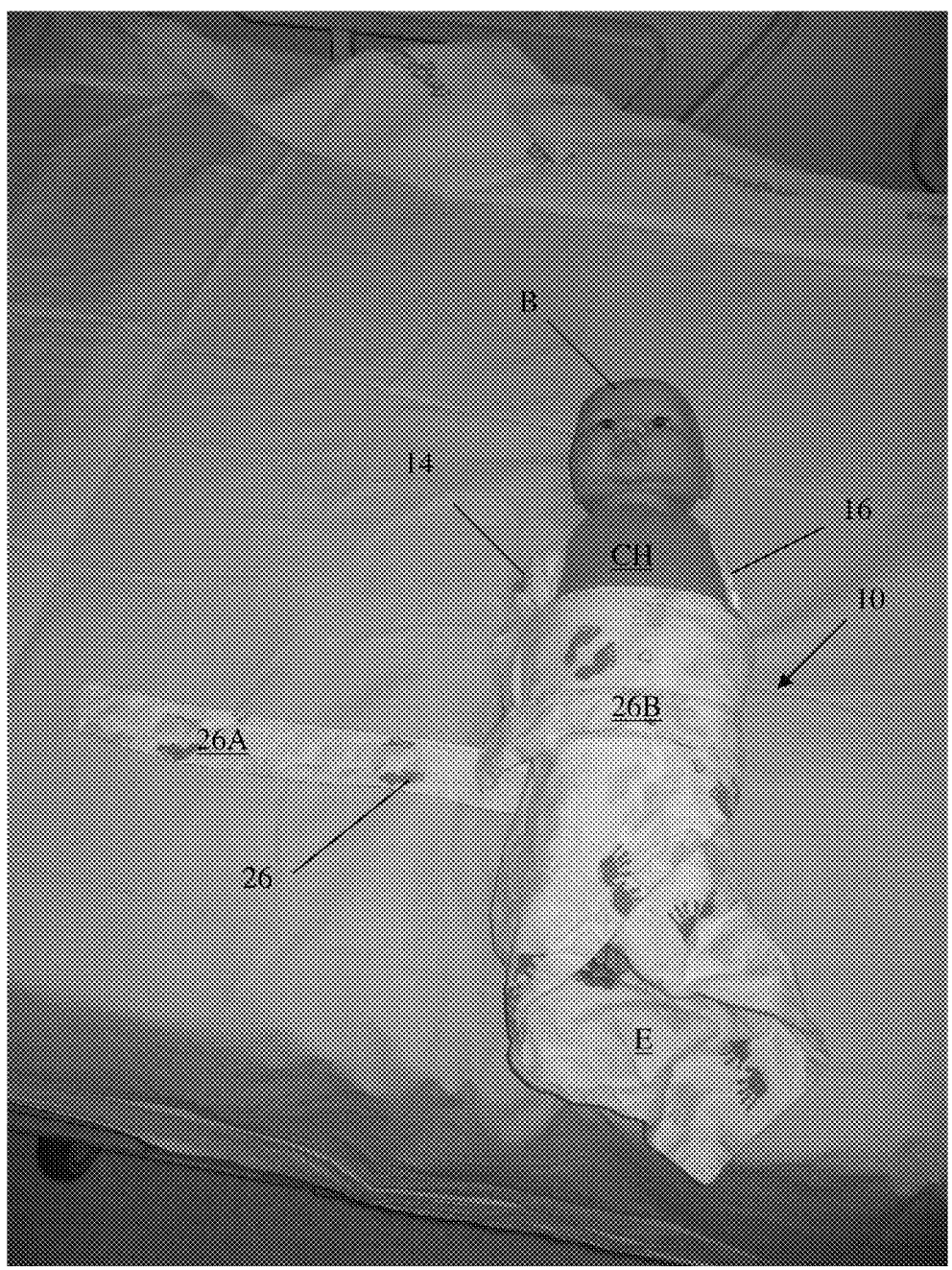

As shown in FIGS. 22, 30 and 31, a strap 26 can optionally be wrapped around the baby B and wrap 10. The strap 26 can be put under the wrapped baby B. A first end 26A can be pulled around the baby B to the front of the baby B so that a first portion of the fastener 28 is exposed. The second end 26B can then be pulled around the baby B so that the second portion of the fastener 28 faces and attaches to the first portion of the fastener 28 as shown in FIG. 22. The strap 26 can be placed over the folded peripheral side portions 30, 32. In this manner, the strap 26 can hold the folded peripheral side portions 30, 32 in place. The strap 26 can be placed around the legs of the baby B that are under the folded peripheral side portions 30, 32. In this manner, the strap 26 can help to prevent the baby B from raising her legs toward her chest CH over the folded peripheral side portions 30, 32.

Instead of or in addition to the strap 26 a fastener can be used to hold the peripheral side portions 30, 32 in place around the baby B. The fastener can be snaps, magnets, adhesives, buttons, hook and loop fasteners, clasps, pins, buckles, or the like. For example, similar to the embodiment shown in FIGS. 21A-21C, a fastener, for example, a hook and loop fastener, can be to hold the peripheral side portions 30, 32 in place. For example, a portion (the hook portion or the loop portion) of the hook and loop fastener can be secured to one or both of the peripheral side portions 30, 32 on the front side of the wrap 10. The other portion of the hook and loop fastener can be secured to the body 12 on the back side of the wrap 10. When wrap 10 is properly wrapped around a baby B, a segment of the portion of the hook and loop fastener on at least one of the peripheral side portions 30, 32 can engage areas of the portion of the hook and loop fastener on the body 12. The engagements hook and loop fastener hold the peripheral side portions 30, 32 in place around the baby B.

Thus, with the method of use of the wrap 10 illustrated in FIGS. 22-31, the baby B can be securely wrapped while still exposing the chest CH of the baby. In this manner, medical procedures that are performed on the chest, such as echocardiograms, upper G.I. procedures, or the like, can be conducted while the baby B is held still. While this method is described with reference to wrap 10 it can also be used in conjunction with other wrap embodiments, for example, wrap 50 described above in reference to FIG. 20.

Many other methods can be performed for folding the wraps disclosed herein, which are contemplated and covered by the present subject matter. The wraps provide a substrate that effectively swaddles a baby in a unique manner that does not necessarily require folding of every portion of the wrap. The wraps can be used for different procedures and depending on the procedure can be folded in a different manner to allow access to various parts of the baby's body. The wraps can be sheet articles. For example, the wraps can be woven, knit, or nonwoven fabrics. It is contemplated that such wraps can also be formed by other sheet articles like paper or film. The wraps can also comprise different components attached together. Alternatively, the wraps can be a single integral piece of material, such as a fabric. Fabric wraps can be made of natural or man-made fibers, yarns or films. Further, the wraps can be disposable or reusable. Thus, a versatile and effective wrap that can swaddle babies for medical procedures or observations is provided.

Embodiments of the present disclosure shown in the drawings and described above are exemplary of numerous embodiments that can be made within the scope of the above disclosure and appending claims. It is contemplated that the configurations of the fabric wraps and methods of use of the same can comprise numerous configurations other than those specifically disclosed.

What is claimed is:

1. A wrap for swaddling babies, the wrap comprising:
   a body having a width and a side having a length, the side defining a side edge;
   a neck extending outward from the side edge of the body along a central axis of the body such that a proximal end of the neck is integral to the body and a distal end of the neck extends away from the body, the neck having a length that is less than the length of the body so that the side edge of the side of the body is formed on either side of the neck with the length of the neck being such that when the body is folded around a baby the neck does not fold around the baby; and
   two arms attached to the neck at the distal end of the neck with the arms extendable outward from the neck in an opposite direction to one another so that the arms are separated from the body by at least a first distance that defines a width of the neck and the arms extend about parallel with each other while also extending about parallel with and along the side edge of the body; and
   the two arms each having a width and a length, the width being less than the width of the body of the wrap and not wide enough to cover a chest region of the baby, the width of the neck, the widths of the arms and the lengths of the arms being sized to work in combination to permit both of the arms of the wrap to be folded downwardly over shoulders of the baby and over arms of the baby but not over the chest region of the baby and to tuck the arms of the wrap between the body of the baby and the body of the wrap to aid in snugly holding and at least partially immobilize the arms and shoulders of the baby while leaving the chest region of the baby exposed after the folding of the body of the wrap around the baby.

2. The wrap according to claim 1, wherein the body comprises a triangular shape having three angled corners with the side edge of the body from which the neck extends comprising a base side edge and the angled corner opposite the base side edge forming an end portion of the body.

3. The wrap according to claim 2, wherein the remaining angled corners of the body form peripheral side portions configured to be folded across a lower torso and legs of a baby.

4. The wrap according to claim 3, further comprising a strap configured to wrap around at least the folded body to further secure the peripheral side portions in their folded positions.

5. The wrap according to claim 3, wherein the end portion of the body is configured to be left unfolded upon the folding of the peripheral side portions to allow access to a body of a baby wrapped within the wrap to permit attachment of a medical device.

6. The wrap according to claim 1, wherein the arms have a combined length that is greater than the length of the side edge of the body along which the arms extend.

7. The wrap according to claim 1, further comprising a strap configured to be placed around the wrap once the wrap is folded around a baby.

8. The wrap according to claim 7, wherein the strap can have a fastener mechanism attached thereto to secure the wrap in place.

9. The wrap according to claim 1, wherein the body, neck and arms comprise a fabric.

10. The wrap according to claim 1, wherein the body, neck and arms comprise an integral piece of fabric.

11. The wrap according to claim 1, wherein the arms include a portion of a fastener on a front side of the wrap that engages another portion of a fastener on the body on the backside of the wrap.

12. A method for swaddling babies during medical procedures and observations, the method comprising:
   providing a wrap comprising:
      (i) a body having a width and a base side defining a side edge and first and second peripheral side portions;
      (ii) a neck extending outward from the base side edge of the body along a central axis of the body such that a proximal end of the neck is integral to the body and a distal end of the neck extends away from the body, the neck having a length that is less than the length of the body so that the side edge of the side of the body is formed on either side of the neck with the length of the neck being such that when the body is folded around a baby the neck does not fold around the baby; and
      (iii) two arms attached at the distal end of the neck along the base side edge of the body with the arms extendable outward in an opposite direction to one another so that the arms are separated from the body by at least a first distance that defines a width of the neck and the arms extend about parallel with each other while also extending about parallel with and along the base side edge of the body; and
      (iv) the two arms each having a width and a length, the width being less than the width of the body of the wrap and not wide enough to cover a chest region of the baby, the width of the neck, the widths of the arms and the lengths of the arms being sized to work together to permit both of the arms of the wrap to be folded downwardly over shoulders of PE the baby and over arms of the baby but not over the chest region of the baby and to tuck the arms of the wrap between the body of the baby and the body of the wrap to aid in snugly holding and at least partially immobilize the arms and shoulders of the baby while leaving the chest region of the baby exposed after the folding of the body of the wrap around the baby;
   placing the wrap in a flat planar position with the arms extending outward in an opposite direction to one another along the base side edge of the body;
   placing a baby on the wrap with shoulders of the baby aligned with the arms of the wrap;

folding the first peripheral side portion over the baby and the second peripheral side portion over the first peripheral side portion; and folding the arms of the wrap diagonally and downward over the shoulders of the baby and over the first and second peripheral side portions so that the arms of the wrap cross.

13. The method according to claim 12, further comprising tucking the arms of the wrap behind the body of the wrap after folding the arms of the wrap.

14. The method according to claim 12, further comprising wrapping a strap around the folded body and arms of the wrap to further secure the peripheral side portions and the arms in their respective folded positions.

15. The wrap according to claim 12, wherein the arms and the body of the wrap include a fastener.

16. The method according to claim 15, further comprising engaging the portion of the fastener on the arms of the wrap with the portion of the fastener on the body on a backside of the wrap to secure the wrap around the baby.

17. A method for swaddling babies during medical procedures and observations, the method comprising:
    providing a wrap comprising:
        (i) a body having a base side and first and second peripheral side portions;
        (iii) two arms attached to the body along the base side of the body, the arms extendable outward from the neck in an opposite direction to one another so that the arms extend parallel with and along the base side of the body;
    placing the wrap in a flat planar position with the arms extending outward in an opposite direction to one another along the base side of the body;
    placing a baby on the wrap with shoulders of the baby aligned with the arms of the wrap; and
    folding the arms of the wrap downward over the shoulders of the baby and over arms of the baby but not over a chest region of the baby and tucking the arms of the wrap between the body of the baby and the body of the wrap so that the chest region of the baby is exposed.

18. The method according to claim 17, further comprising folding the first peripheral side portion of the body of the wrap over the baby and the second peripheral side portion of the body of the wrap over the first peripheral side portion of the body of the wrap.

19. The method according to claim 17, further comprising wrapping a strap around the folded peripheral side portions of the body of the wrap to further secure the peripheral side portions in their folded positions.

20. The method according to claim 17, further comprising pulling ends of the folded arms of the wrap in a direction away from the baby to snugly tighten the arms of the wrap around shoulder and arms of the baby.

* * * * *